(12) United States Patent
Kim

(10) Patent No.: US 7,321,783 B2
(45) Date of Patent: Jan. 22, 2008

(54) MOBILE ENTERTAINMENT AND COMMUNICATION DEVICE

(75) Inventor: Ki Il Kim, Los Angeles, CA (US)

(73) Assignee: Minerva Industries, Inc., Los Angeles, CA (US)

( * ) Notice: Subject to any disclaimer, the term of this patent is extended or adjusted under 35 U.S.C. 154(b) by 199 days.

(21) Appl. No.: 10/719,363

(22) Filed: Nov. 20, 2003

(65) Prior Publication Data

US 2004/0110545 A1    Jun. 10, 2004
US 2006/0229114 A2    Oct. 12, 2006

Related U.S. Application Data

(63) Continuation of application No. 09/531,356, filed on Mar. 20, 2000, now Pat. No. 6,681,120, which is a continuation-in-part of application No. 08/846,108, filed on Apr. 25, 1997, now Pat. No. 6,278,884.

(30) Foreign Application Priority Data

Oct. 15, 1999   (KR)   ........................ 20-199-0022160
Dec. 17, 1999   (KR)   ........................ 20-199-0028580

(51) Int. Cl.
*H04M 1/00* (2006.01)
*H04Q 7/20* (2006.01)

(52) U.S. Cl. .................. 455/556.1; 455/90.1; 455/557; 455/558; 455/404.1; 455/456.1

(58) Field of Classification Search .. 455/404.1–404.2, 455/41.2, 556.1–556.2, 557, 558, 575, 1, 455/456.1, 575.2, 569, 90.1; 340/539.1, 340/539, 502, 504, 514; 709/231, 232; 379/442, 379/433.09, 433.05, 428.01, 420.01
See application file for complete search history.

(56) References Cited

U.S. PATENT DOCUMENTS 4,148,070 A    4/1979 Taylor .................... 358/160

(Continued)

FOREIGN PATENT DOCUMENTS

DE           38 39 959 C2    4/1990

(Continued)

OTHER PUBLICATIONS

Sternglass, "The Future is in the PC Cards", Databook Inc. IEEE Spectrum. Jun. 1992, pp. 46-50.

(Continued)

*Primary Examiner*—Erika A. Gary
(74) *Attorney, Agent, or Firm*—Connolly Bove Lodge & Hutz LLP

(57) ABSTRACT

A mobile entertainment and communication device in a palm-held size housing has a cellular or satellite telephone capable of wireless communication with the Internet and one or more replaceable memory card sockets for receiving a blank memory card for recording data directly from the Internet and, in particular, musical performances that then can be selectively reproduced by the device for the enjoyment of the user, including both audio and visual recordings and reproductions. The device also includes a camera and microphone for recording images and sound within the range of the device that can be wirelessly transmitted, either selectively or automatically to a remote telephone. Further, the device includes sensors for sensing unusual conditions that may also be transmitted to a remote telephone, together with the location of the device as determined by a GPS section of the device.

125 Claims, 2 Drawing Sheets

U.S. PATENT DOCUMENTS

| | | | | |
|---|---|---|---|---|
| 4,302,776 | A | 11/1981 | Taylor et al. | 358/160 |
| 4,481,382 | A | 11/1984 | Villa-Real | 179/2 |
| 4,591,661 | A | 5/1986 | Benedetto et al. | 179/2 |
| 4,821,121 | A | 4/1989 | Beaulier | 358/160 |
| 4,825,457 | A | 4/1989 | Lebowitz | 379/40 |
| 4,962,521 | A | 10/1990 | Komatsu et al. | 379/53 |
| 5,003,576 | A | 3/1991 | Helferich | 379/67.1 |
| 5,063,587 | A | 11/1991 | Semasa et al. | 348/14.14 |
| 5,144,661 | A | 9/1992 | Shamosh et al. | 348/143 |
| 5,189,632 | A | 2/1993 | Paajanen et al. | 364/705.05 |
| 5,243,640 | A | 9/1993 | Hadley et al. | 455/426 |
| 5,257,007 | A | 10/1993 | Steil et al. | 340/539.3 |
| 5,257,414 | A * | 10/1993 | Trahan et al. | 455/558 |
| 5,334,974 | A | 8/1994 | Simms et al. | 340/990 |
| 5,335,276 | A | 8/1994 | Thompson et al. | 380/21 |
| 5,343,509 | A | 8/1994 | Dounies | 379/40 |
| 5,353,330 | A * | 10/1994 | Fujiwara | 455/563 |
| 5,382,943 | A | 1/1995 | Tanaka | 340/539 |
| 5,418,837 | A | 5/1995 | Johansson et al. | 379/58 |
| 5,420,573 | A * | 5/1995 | Tanaka et al. | 340/825.24 |
| 5,463,595 | A | 10/1995 | Rodhall et al. | 367/93 |
| 5,485,504 | A | 1/1996 | Ohnsorge | 379/58 |
| 5,487,182 | A | 1/1996 | Hansson | 455/569.1 |
| 5,491,507 | A | 2/1996 | Umezawa et al. | 348/14 |
| 5,499,286 | A | 3/1996 | Kobayashi | 455/563 |
| 5,504,812 | A | 4/1996 | Vangarde | 379/430 |
| 5,515,043 | A | 5/1996 | Berard et al. | 340/988 |
| 5,515,285 | A | 5/1996 | Garrett, Sr. et al. | 701/300 |
| 5,517,547 | A | 5/1996 | Ladha et al. | 379/40 |
| 5,535,274 | A * | 7/1996 | Braitberg et al. | 379/446 |
| 5,537,608 | A | 7/1996 | Beatty et al. | 379/158 |
| 5,546,072 | A | 8/1996 | Creuseremee et al. | 340/574 |
| 5,550,754 | A * | 8/1996 | McNelley et al. | 348/14.01 |
| 5,555,286 | A * | 9/1996 | Tendler | 455/404.2 |
| 5,568,535 | A | 10/1996 | Sheffer et al. | 379/39 |
| 5,584,052 | A | 12/1996 | Gulau et al. | 455/79 |
| 5,587,701 | A | 12/1996 | Hess | 340/541 |
| 5,590,417 | A | 12/1996 | Rydbeck | 455/89 |
| 5,613,222 | A * | 3/1997 | Guenther | 455/575.2 |
| 5,615,384 | A | 3/1997 | Allard et al. | 395/800 |
| 5,630,205 | A | 5/1997 | Ekelund | 455/412.1 |
| 5,640,675 | A | 6/1997 | Pinault et al. | 455/33.1 |
| 5,657,371 | A * | 8/1997 | Suomi et al. | 455/418 |
| 5,666,159 | A | 9/1997 | Parulski et al. | 348/211 |
| 5,687,216 | A | 11/1997 | Svensson | 379/58 |
| 5,699,406 | A * | 12/1997 | Liikanen et al. | 455/558 |
| 5,712,619 | A | 1/1998 | Simkin | 340/539 |
| 5,717,379 | A * | 2/1998 | Peters | 340/539.25 |
| 5,726,660 | A | 3/1998 | Purdy et al. | 342/357.1 |
| 5,729,197 | A | 3/1998 | Cash | 340/539.3 |
| 5,737,491 | A | 4/1998 | Allen et al. | 704/270 |
| 5,740,543 | A | 4/1998 | Maeda | 455/550 |
| 5,742,666 | A | 4/1998 | Alpert | 379/58 |
| 5,742,845 | A | 4/1998 | Wagner | 395/831 |
| 5,748,081 | A | 5/1998 | Lin | 340/555 |
| 5,768,533 | A | 6/1998 | Ran | 395/200 |
| 5,787,399 | A | 7/1998 | Lee et al. | 704/270 |
| 5,790,957 | A | 8/1998 | Heidari | 455/553 |
| 5,793,419 | A | 8/1998 | Fraley | 348/143 |
| 5,806,005 | A | 9/1998 | Hull et al. | 455/566 |
| 5,808,564 | A | 9/1998 | Simms et al. | 340/990 |
| 5,815,201 | A | 9/1998 | Hashimoto et al. | 348/232 |
| 5,815,426 | A * | 9/1998 | Jigour et al. | 365/51 |
| 5,819,172 | A | 10/1998 | Campana, Jr. et al. | 455/412 |
| 5,870,710 | A | 2/1999 | Ozawa et al. | 704/500 |
| 5,884,168 | A | 3/1999 | Kolev et al. | 455/432 |
| 5,893,037 | A | 4/1999 | Reele et al. | 455/556 |
| 5,894,597 | A | 4/1999 | Schwartz et al. | 455/558 |
| 5,910,815 | A | 6/1999 | Boursier et al. | 348/14 |
| 5,914,675 | A | 6/1999 | Tognazzini | 455/563 |
| 5,914,941 | A | 6/1999 | Janky | 370/313 |
| 5,917,542 | A | 6/1999 | Moghadam et al. | 348/207 |
| 5,924,044 | A | 7/1999 | Vannatta et al. | 455/556 |
| 5,926,210 | A | 7/1999 | Hackett et al. | 348/158 |
| 5,933,328 | A | 8/1999 | Wallace et al. | 361/737 |
| 5,937,341 | A | 8/1999 | Suominen | 455/324 |
| 5,943,603 | A | 8/1999 | Parulski et al. | 455/3.1 |
| 5,953,322 | A | 9/1999 | Kimball | 370/328 |
| 5,957,718 | A | 9/1999 | Cheng et al. | 439/347 |
| 5,963,245 | A | 10/1999 | McDonald | 348/14 |
| 5,969,750 | A | 10/1999 | Hsieh et al. | 348/14.1 |
| 5,991,637 | A | 11/1999 | Mack, II et al. | 340/989 |
| 6,002,326 | A | 12/1999 | Turner | 340/426 |
| 6,002,946 | A | 12/1999 | Reber et al. | 455/557 |
| 6,006,109 | A * | 12/1999 | Shin | 455/557 |
| 6,009,336 | A | 12/1999 | Harris et al. | 455/566 |
| 6,011,967 | A | 1/2000 | Wieck | 455/404 |
| 6,014,573 | A | 1/2000 | Lehtonen et al. | 455/569 |
| 6,046,730 | A | 4/2000 | Bowen et al. | 345/168 |
| 6,049,273 | A | 4/2000 | Hess | 340/539.11 |
| 6,069,648 | A | 5/2000 | Suso et al. | 348/14 |
| 6,073,034 | A | 6/2000 | Jacobsen et al. | 455/566 |
| 6,081,708 | A | 6/2000 | Vasnier | 455/426 |
| 6,085,112 | A | 7/2000 | Kleinschmidt et al. | 455/556 |
| 6,101,372 | A * | 8/2000 | Kubo | 455/558 |
| 6,109,797 | A | 8/2000 | Nagura et al. | 385/88 |
| 6,111,604 | A | 8/2000 | Farris et al. | 455/412 |
| 6,122,526 | A | 9/2000 | Parulski et al. | 455/556 |
| 6,137,525 | A * | 10/2000 | Lee et al. | 348/14.02 |
| 6,144,657 | A | 11/2000 | Baehr | 370/352 |
| 6,167,253 | A | 12/2000 | Farris et al. | 455/412 |
| 6,195,531 | B1 | 2/2001 | Aguirre et al. | 455/11.1 |
| 6,199,756 | B1 | 3/2001 | Kondo et al. | |
| 6,211,649 | B1 | 4/2001 | Matsuda | 320/115 |
| 6,219,560 | B1 | 4/2001 | Erkkila et al. | 455/557 |
| 6,243,596 | B1 * | 6/2001 | Kikinis | 455/572 |
| D444,473 | S | 7/2001 | Okamoto et al. | D14/436 |
| D445,111 | S | 7/2001 | Okamoto et al. | D14/436 |
| 6,278,884 | B1 | 8/2001 | Kim | 455/556 |
| D447,481 | S | 9/2001 | Wallace et al. | D14/432 |
| 6,295,206 | B1 | 9/2001 | Kondo et al. | 361/736 |
| 6,310,609 | B1 | 10/2001 | Morgenthaler | 345/170 |
| 6,323,064 | B1 | 11/2001 | Lee et al. | 438/117 |
| D452,865 | S | 1/2002 | Wallace et al. | D14/435 |
| D453,934 | S | 2/2002 | Wallace et al. | D14/435 |
| 6,361,369 | B1 | 3/2002 | Kondo et al. | |
| 6,366,614 | B1 | 4/2002 | Pian et al. | 375/240.02 |
| 6,392,697 | B1 | 5/2002 | Tanaka et al. | 348/220.1 |
| 6,396,931 | B1 | 5/2002 | Malilay | 381/67 |
| D459,355 | S | 6/2002 | Shimoda et al. | D14/436 |
| 6,408,351 | B1 | 6/2002 | Hamdi et al. | 710/1 |
| 6,423,892 | B1 | 7/2002 | Ramaswamy | 84/609 |
| 6,427,078 | B1 | 7/2002 | Wilska et al. | 455/550.1 |
| 6,473,631 | B1 | 10/2002 | Siddoway et al. | 455/575 |
| 6,480,724 | B1 | 11/2002 | Erkkila et al. | 455/557 |
| D467,586 | S | 12/2002 | Shimoda et al. | D14/435 |
| 6,491,541 | B2 | 12/2002 | Wakino | 439/451 |
| 6,498,809 | B1 | 12/2002 | Dean et al. | 375/240 |
| 6,519,241 | B1 | 2/2003 | Theimer | 370/338 |
| 6,531,982 | B1 | 3/2003 | White et al. | 342/357.09 |
| 6,553,238 | B1 | 4/2003 | Ginzel et al. | 455/557 |
| 6,573,938 | B1 | 6/2003 | Schulz et al. | 348/373 |
| 6,590,303 | B1 | 7/2003 | Austin et al. | 307/119 |
| 6,606,109 | B1 | 8/2003 | Ito et al. | 347/208 |
| 6,611,907 | B1 | 8/2003 | Maeda et al. | 711/170 |
| 6,616,053 | B2 | 9/2003 | Kondo et al. | |
| 6,634,561 | B1 | 10/2003 | Wallace | 235/492 |
| 6,640,109 | B1 | 10/2003 | Drozt et al. | 455/508 |
| 6,650,913 | B1 | 11/2003 | Hayashi | 455/575.3 |
| 6,678,514 | B2 | 1/2004 | Wheeler et al. | 455/404.1 |
| 6,681,120 | B1 * | 1/2004 | Kim | 455/556.1 |
| 6,687,515 | B1 | 2/2004 | Kosaka | 455/566 |
| 6,694,200 | B1 | 2/2004 | Naim | 700/94 |
| 6,729,548 | B2 | 5/2004 | Kondo et al. | |

| | | | |
|---|---|---|---|
| 6,738,423 B1 | 5/2004 | Lainema et al. | 375/340.03 |
| 6,768,645 B2 | 7/2004 | Kadonaga | 361/737 |
| 6,781,925 B2 | 8/2004 | Nuovo | 369/11 |
| 6,783,076 B2 | 8/2004 | Kondo et al. | |
| D496,632 S | 9/2004 | David et al. | D13/147 |
| 6,867,485 B2 | 3/2005 | Wallace | 257/679 |
| 6,919,923 B1 | 7/2005 | Tanaka et al. | 348/220.1 |
| 6,922,343 B2 | 7/2005 | Nakanishi et al. | 361/737 |
| 6,957,073 B2 | 10/2005 | Bye | 455/456.1 |
| 6,999,802 B2 | 2/2006 | Kim | 455/575.1 |
| 7,006,146 B1 | 2/2006 | Tanaka et al. | 348/376 |
| 7,027,840 B2 | 4/2006 | McKee et al. | 455/567 |
| 7,048,197 B2 | 5/2006 | Nishizawa et al. | 235/492 |
| 7,065,342 B1 | 6/2006 | Rolf | 455/412.1 |
| 7,068,782 B2 | 6/2006 | Mueller et al. | 379/433.1 |
| 7,123,936 B1 | 10/2006 | Rydbeck et al. | 455/557 |
| 7,149,471 B1 | 12/2006 | Arisawa et al. | 455/3.04 |
| 7,184,092 B2 | 2/2007 | Lim | 348/376 |

FOREIGN PATENT DOCUMENTS

| | | |
|---|---|---|
| DE | 38 39 959 C2 | 11/1991 |
| DE | 41 26105 A1 | 2/1993 |
| DE | 43 25 588 A1 | 2/1995 |
| DE | 43 35 773 A1 | 4/1995 |
| DE | 43 44 753 A1 | 6/1995 |
| DE | 44 15 090 A1 | 11/1995 |
| DE | 195 05 486 A1 | 8/1996 |
| DE | 196 03 747 C1 | 1/1997 |
| DE | 196 06 747 C1 | 1/1997 |
| DE | 19523227 | 1/1997 |
| DE | 195 32 103 A1 | 3/1997 |
| DE | 19806508 A1 | 8/1999 |
| EP | 0 830 000 * | 3/1998 |
| GB | 2 256 771 | 12/1992 |
| GB | 230875 | 7/1997 |
| JP | 3-109891 | 5/1991 |
| JP | 6268582 A | 9/1994 |
| JP | 07111640 | 4/1995 |
| JP | 8294030 A | 11/1996 |
| JP | 10192483 A | 7/1998 |
| WO | 95/20271 | 7/1995 |
| WO | WO-96/38762 A1 | 12/1996 |

OTHER PUBLICATIONS

"A Portable Multimedia Terminal", IEEE Communication Magazine—Dec. 1992.

06268582—English Patent Abstract of Japan Publication.

6133081—English Patent Abstract of Japan Publication.

Published User Guide for Samsung SCH-1500 mobile phone ("Samsung") no date.

Article "Japanese trio unveil MP3-on-cellphone system" on *The Register* web site www.the register.co.uk/1999/12/14 (3 pgs.).

Office Action mailed Apr. 9, 2007 in Kim U.S. Appl. No. 10/773,606, filed Feb. 6, 2004.

Response to Non-final Office Action dated Apr. 9, 2007 in Kim U.S. Appl. No. 10/733,606, filed Feb. 6., 2004.

Supplemental Response to Non-Final Office Action dated Apr. 9, 2007 in Kim U.S. Appl. No. 10/733,606, filed Feb. 6, 2004.

Office Action mailed Feb. 8, 2007 in Kim U.S. Appl. No. 1/773,606, filed Feb. 6, 2004.

Response to Office Action mailed Feb. 8, 2007 Kim U.S. Appl. No. 10/773,606, filed Feb. 6, 2004.

Office Action mailed Aug. 11, 2006 in Kim U.S. Appl. No. 11/184,297, filed Jul. 18, 2005.

Amendment filed Aug. 25, 2006 in Kim U.S. Appl. No. 11/184,297, filed Jul. 18, 2005.

Office Action mailed Oct. 26, 2006 in Kim U.S. Appl. No. 11/184,297, filed Jul. 18, 2005.

Request for Continued Examination and Amendment filed Nov. 10, 2006 in Kim U.S. Appl. No. 11/184,297, filed Jul. 18, 2005.

Office Action mailed Mar. 2, 2007 in Kim U.S. Appl. No. 11/184,297, filed Jul. 18, 2005.

Amendment filed Mar. 12, 2007 in Kim U.S. Appl. No. 11/184,297, filed Jul. 18, 2005.

Supplemental Amendment filed Jun. 28, 2007 in Kim U.S. Appl. No. 11/184,297, filed Jul. 18, 2005.

Second Supplemental Amendment filed Jul. 24, 2007 in Kim U.S. Appl. No. 11/184,297, filed Jul. 18, 2005.

Notice of Allowance mailed Mar. 22, 2001 in U.S. Appl. No. 08/846,108, filed Apr. 25, 1997.

Minerva Industries, Inc. v. Motorola, Inc. et al., Civil Action No. 2-07CV-299, Eastern District of Texas Complaint, filed Jun. 6, 2007.

Minerva Industries, Inc. v. Research In Motion Corporation et al., Civil Action No. 2-07CV-230, Eastern District of Texas - Complaint, filed Jun. 6, 2007.

Final Office Action mailed Oct. 26, 2007 in Kim U.S. Appl. No. 11/184,297, filed Jul. 18, 2005.

* cited by examiner

MOBILE ENTERTAINMENT AND COMMUNICATION DEVICE

This is a Continuation of application Ser. No. 09/531,356, filed Mar. 20, 2000, now U.S. Pat. No. 6,681,120, which was a Continuation-In-Part of application Ser. No. 08/846,108, filed Apr. 25, 1997, now U.S. Pat. No. 6,278,884, which is incorporated in this application in full by this reference.

This invention relates to a mobile entertainment and communication device that is readily carried by a person and provides numerous conveniences and features including, but not limited to, a cellular or satellite telephone with access to the Internet.

A principle object of this invention is to provide a personal entertainment and communication device that is portable and includes a cellular or satellite accessible telephone with the ability to access the internet, replaceable memory cards for downloading data from the internet, and means for reproducing such data on the device from the cards. Specifically, the device of this invention is particularly adapted to download music, images or other data in a wireless manner from the Internet and selectively reproduce such music, images or other data from replaceable memory cards for one's personal enjoyment or other use.

Still another object of the present invention is to provide a mobile entertainment and communication device that wirelessly records data from the Internet and selectively reproduces that data, such as music and/or images, and also provides a portable security device capable of automatically communicating with a remote telephone and transmitting emergency data including sounds, pictures, location and similar information when selectively activated by the owner or when automatically activated by conditions sensed by integral sensors, including conditions such as sudden movement, sounds, light, heat, smoke or the like.

Other and more detailed objects and advantages of the present invention will readily appear to those skilled in the art from the detailed description and accompanying drawings of the preferred embodiments, wherein.

Figures 1, 2, 3, 4:
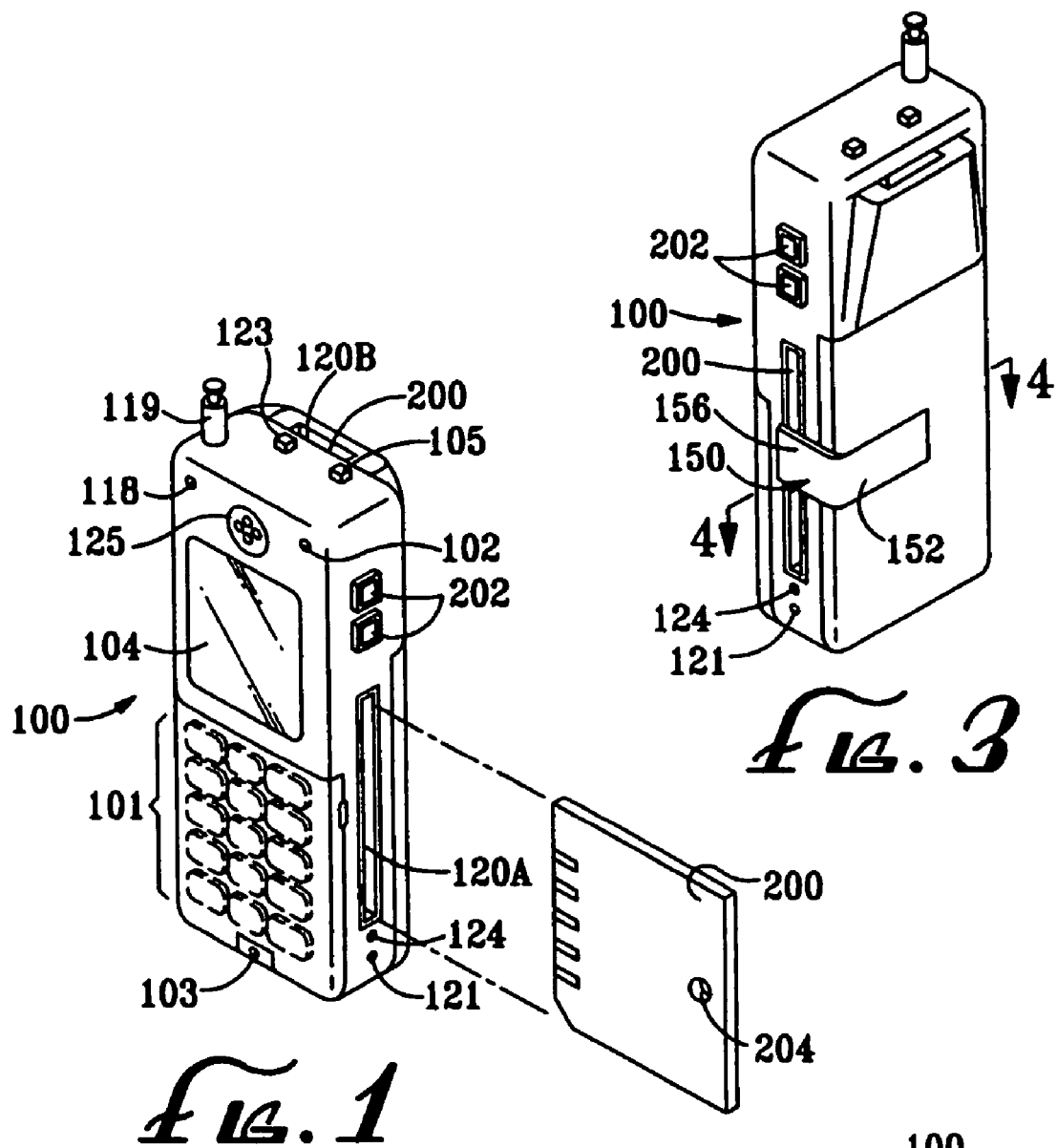
FIG. 1 is a perspective view of the front of the entertainment and communication device of the present invention.
FIG. 2 is a perspective view of a replaceable memory card for use with the device illustrated in FIG. 1.
FIG. 3 is a perspective view of the back of the entertainment and communication device of the present invention showing an optional card latching device.
FIG. 4 is a sectional view of the device taken on the line 4-4 in FIG. 3.
Figure 5:
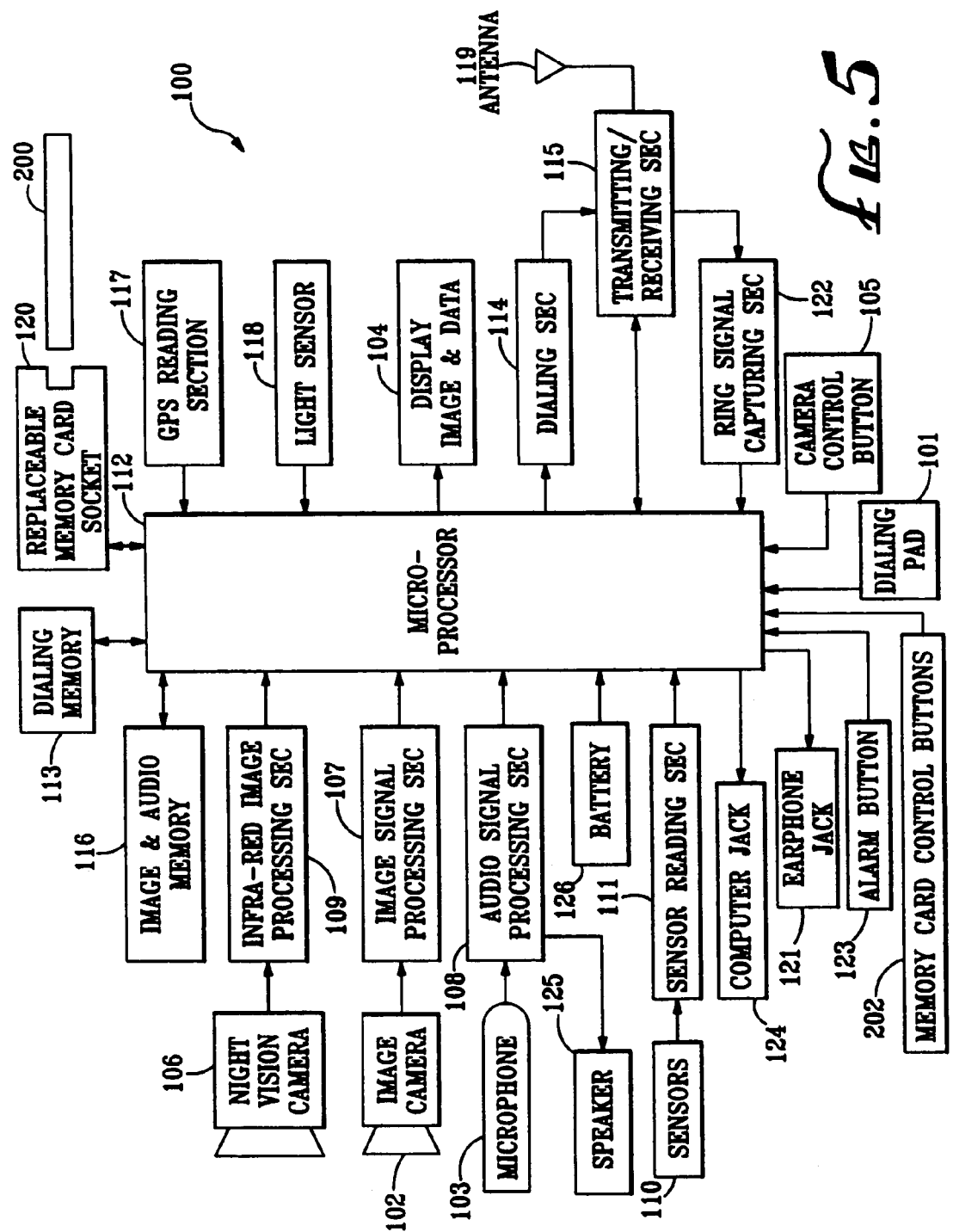
FIG. 5 is a schematic drawing of the components of the entertainment and communication device shown in FIGS. 1 and 2.

Referring more particularly to the figures, the entertainment and communication device, generally designated 100, includes a cellular telephone or satellite accessible telephone or the like, hereinafter referred to collectively as a "cellphone", having a dialing pad 101 with push buttons for operating the cell phone in a substantially conventional manner and also for controlling the operation of other components of the device 100. The cellphone includes a microphone 103 and a speaker 125 for using the cellphone as a telephone for verbal communications. A display panel 104 is provided on the front of the device 100 for displaying images and data, including but not limited to the conventional data displayed for the use of the cellphone. The cellphone also includes a dialing memory 113, a dialing section 114, a transmitting/receiving section 115, an antenna 119 and a ring signal capturing section 122. The microphone 103 and speaker 125 are connected through an audio signal processing section 108 to the microprocessor 112 of the device 100. The dialing memory 113, dialing section 114, transmitting/receiving section 115, ring signal capturing section 122 and dialing pad 101 are also connected to the microprocessor 112 for operating the cellphone in a conventional manner, through the microprocessor 112.

The cellphone of the entertainment and communication device 100 is of the type that is capable of making a wireless connection to the Internet for receiving data therefrom and transmitting data thereto, such as the Samsung® Model No. 3500, Qualcom® No. 1960, Sprint® PCS, or the like, without a hardwire connection through a personal computer or telephone line.

The entertainment and communication device 100 of the present invention is provided with a socket 120 for receiving a replaceable memory card 200. The opening for the socket 120 may be provided on the side of the device 100, as shown at 120A, or at one end of the device 100, as shown at 120B, or both. The memory card 200 is provided with electrical contacts 201 (see FIG. 2) which are adapted to engage corresponding electrical contacts (not shown) in the socket 120, which contacts in turn are connected to the microprocessor 112 for communication between the replaceable memory card 200 and the microprocessor 112. The memory card 200 may be a prerecorded card or a flash (blank) card suitable for recording data from the microprocessor 112. By appropriately operating the cellphone to connect to or access the Internet and then operating the memory card control buttons 202, data from the Internet may be recorded on the replaceable memory card 200, such as musical performances, images (still or moving), written text or the like (hereinafter referred to as "data"). In addition to the audio data, the musical performance data from the Internet may include images of the performers or the like, and/or the words of the musical performance. Other audio and visual data also may be downloaded from the Internet to memory card 200. Subsequent to the recordation of the musical performance or other data on the replaceable memory card 200 or upon the positioning of a prerecorded memory card 200 in a socket 120, the memory card control buttons 202 may be manipulated to reproduce the musical performance or other data with the sound being broadcast by the speaker 125 or to earphones (not shown) connected to the earphone jack 121 or transmitted to wireless earphones (not shown). The device 100 also includes controls, such as on dialing pad 101 or separately, for controlling the music volume, balance, selection (skip), equalization and the like. The images and/or words included in the recording on a memory card 200 will be displayed on the display panel 104.

The memory card 200 is preferably of a high memory capacity and a size to fit substantially inside the housing of the device 100 so as not to protrude therefrom and yet be of substantially the full width of the device 100 to maximize the memory capacity of the card 200 substantially beyond the memory capacity of conventional prerecorded memory cards, such as for MP3 players. Of course, the width of the device 100 is limited from a practical standpoint to a width that is comfortable in the palm of an adult person's hand for use as a telephone. Thus, as a practical matter, the width of the memory card is limited to about 1½" to 2". Similarly, the overall size of the device 100 must be sufficiently small to be comfortably carried in a pocket or purse to be most practical. Further, while the thickness of the card 200 may be increased somewhat for increasing the memory capacity there is also a practical limit to that increased thickness so that the thickness of the device 100 does not become excessive, but it is contemplated that memory cards 200 of about twice the thickness may be provided and interchangeably installed in the socket 120 for at least doubling the memory capacity or separate sockets, such as sockets 120A and 120B, may be provided for accommodating memory cards 200 of different thicknesses. Still further, the length of the device 100 is limited to a practical length and, therefore, the vertical length of the card is similarly limited. The card 200 and socket 120 may be provided with matching non-symmetrical shapes, grooves, ridges or the like for requiring the card 200 to be inserted into the socket in the correct orientation, such as the cutoff corner of card 200 shown in FIG. 1 (lower left) and FIG. 2 (lower right). The device 100 may also be provided with an integral image and audio storage memory 116 connected to the microprocessor for temporary or permanent storage of data, in addition to data storage on cards 200, and the data stored on memory 116 may be reproduced in the same manner as from replaceable memory cards 200.

Referring more particularly to FIGS. 3 and 4, a latching device, generally designated 150, is shown for retaining the replaceable memory card 200 in the socket 120A and for facilitating the removal of the memory card 200 from the socket 120A. The latching device 150 includes a lever 152 pivotally connected at 154 to the back of the housing of the device 100, with a tab 156 extending along the side of the device and over a portion of the socket 120A in the closed position. A pin 158 extends inwardly from the lever 152 and engages a hole 204 in the memory card 200. When the latching device 150 is pivoted to the open position shown in dashed lines in FIG. 4, the memory card 200 may be readily removed from socket 120A by placing a finger on the portion of the card 200 exposed by opening the latching device 150 or by engaging the hole 204 with a finger nail or a pointed implement, such as a pencil or pen. Further, the pin 158 and hole can be sized and relatively positioned such that the pin 158 urges the card 200 outwardly upon opening the latching device. Still further, the socket 120A may be provided with a spring for urging the card 200 outwardly as soon as the card is unlatched. Of course either the tab 156 or pin 158 may be omitted since the other (pin or tab, respectively) will retain the card 200 in the socket 120A. The latching device 150 may be of a width to only cover a portion of the socket 120A, as shown, or of a width to cover the entire socket (not shown).

Since the device 100 can be wirelessly connected to the internet, it is also possible to use the device 100 for any other Internet functions, such as sending and receiving e-mail, conducting ebusiness, etc. Further, in view of the recording capability of the device 100, the telephone conversations on the cellphone may be selectively recorded (one or both sides) and the device can be used for any sound recording, such as for dictation or face-to-face conversations or conferences. Still further, the microprocessor 112 includes means for automatically interrupting the playing of any musical performance being reproduced on the device 100 when a telephone call is placed or received on the cellphone until the call is completed.

All of the aforedescribed functions and those described hereinafter are powered by a battery means (not shown) in the device 100 which preferably is a single rechargeable battery.

The entertainment and communication device 100 is also provided with a computer jack 124 connected to the microprocessor for selectively connecting the device 100 directly to a computer, radio, television or CD, DVD, VCR, tape or phonograph record player (not shown) by a hard wire (not shown) for downloading and uploading (where appropriate) to and from the replaceable memory card 200 or fixed memory 116 in the device 100.

The entertainment and communication device 100 is also provided with various other features for the personal entertainment, communication, security, safety and the like of the person at all times that the person has the device 100 with him or her. A video camera 102 is connected through an image signal processing section 107 to the microprocessor 112 and the camera operation is controlled by button 105, whereby images may be displayed on the panel 104, recorded on either the integral memory 116 or the replaceable memory card 200, or transmitted by the cellphone to a remote telephone which may be located at a police station, security office, one's own personal computer or the like. The video camera 102 is preferably a digital camera for electronically capturing images, either still or moving, for minimizing the size and battery power requirements, but also may be an analog type camera. Similarly, an infrared night vision camera 106 may be provided and connected to the microprocessor 112 through an infrared image processing section 109 to record or transmit images in the same manner as video camera 102, and a light sensor 118 is connected to the microprocessor 112 for automatically selecting the operation of the night vision 106 when the ambient light is at a very low level. Cameras 102 and 106 will be referred to generically as a "camera". The microphone 103 may also be activated manually or automatically by the microprocessor 112 when either of the cameras 102 or 106 are activated for recording and/or transmitting sounds within the range of the device 100 synchronously with the recording or transmission of images by one of the cameras.

The entertainment and communication device also includes various emergency features for use by the person carrying the device. An alarm button 123 is provided and may be activated to produce an audible alarm from the speaker 125 for dissuading an attacker or intruder or activating a silent alarm whereby the cellphone is automatically operated to communicate the emergency condition to a remote telephone, such as by dialing "911" or a private security telephone number or the like. Similarly, one or more sensors 110, such as motion, infrared, ultrasonic, acceleration, sound, light, heat, smoke, carbon monoxide, poisonous gas or the like sensors, are provided with the device 100 and selectively activated for providing either an audible or silent alarm, similar to the functions of the panic alarm button 123 but without requiring operator activation, and the sensors 110 are connected through the sensor reading section 111 to the microprocessor 112 for using any of the functions of the device 100. For example, with the acceleration sensor of sensors 110 activated while a person has the device 100 in an automobile, the sudden deceleration of the automobile in an accident condition would be sensed by the acceleration sensor to cause the microprocessor 112 to dial an appropriate telephone number stored in the dialing memory 113, such as a "911" or a vehicle rescue number, and transmit the emergency as well as the location of the device 100 as determined by a global positioning satellite (GPS) reading section 117 provided with the device, which GPS reading section 117 may also be activated by the panic alarm 123. Further, if the motion sensor or similar sensors 110 are activated and the device 100 is appropriately positioned, for example in a hotel room, the motion and/or presence of an intruder will be sensed and communicated through the sensor reading section 111 to the microprocessor 112 to activate any desired function, such as an audible alarm from the speaker 125, an automatic dialing of a "911" number, operation of electronic camera 102 or infrared camera 106, operation of the microphone 103, operation of the GPS reading section 117 or the like. Similar functions can be performed by the device 100 when any of the other sensors are activated to sense a particular condition, such as heat, smoke, carbon monoxide, poisonous gas or the like. AM/FM radio receivers can optionally be included for entertainment when the alarm system is not in use. The alarm and radio function components can be mounted on the same printed circuit board within housing 100 or on separate circuit boards.

Thus, by this invention a palm-sized device provides wireless communication with the Internet for downloading musical and visual entertainment onto a high capacity memory card that is replaceable with other prerecorded or downloaded memory cards, and numerous other communication, security, safety and similar functions are selectively available to the user.

What is claimed is:

1. A mobile entertainment and communication device for communicating with the Internet and remotely located telephones, comprising:
   a housing of a palm-held size;
   a cellphone provided in said housing, said cellphone adapted for selectively and wirelessly connecting to the Internet and remotely located telephones and adapted for controlling selection of at least one of (1) downloading data or uploading data from or to the Internet, or (2) downloading data to a computer or other electronic device and said cellphone having at least one of (1) voice controlled dialing, (2) a wireless earphone or (3) a wire connection jack earphone with a microphone for operation of the mobile entertainment and communication device;
   a memory operatively connected to said cellphone;
   a microprocessor operatively connected to said memory;
   said microprocessor adapted for storing data to said memory that is received from the Internet or a remotely located telephone; and
   a display panel operatively connected to said microprocessor, said display panel adapted for reproducing images or other data from at least one of said memory or the Internet, said other data including at least one of moving images, combined sounds and moving images, or music with or without images.

2. A mobile entertainment and communication device for communicating with the Internet and remotely located telephones, comprising:
   a housing of a palm-held size;
   a cellphone provided in said housing, said cellphone adapted for selectively and wirelessly accessing the Internet and remotely located telephones and adapted for controlling selection of at least one of (1) downloading data or uploading data from or to the Internet, or (2) downloading data to a computer or other electronic device and said cellphone having at least one of (1) voice controlled dialing, (2) a wireless earphone or (3) a wire connection jack earphone with a microphone, for operation of the mobile entertainment and communication device;
   a memory operatively connected to said cellphone;
   a microprocessor operatively connected to said memory;
   said microprocessor adapted for causing data stored in said memory or received by said cellphone to be transmitted by said cellphone to the Internet or a remotely located telephone, respectively; and
   a display panel operatively connected to said microprocessor, said display panel adapted for reproducing images or other data from at least one of said memory or the Internet, said other data including at least one of moving images, combined sounds and moving images, or music without images.

3. The device of claim 1 or 2 further comprising
   a speaker operatively coupled to the microprocessor for reproducing sounds from said memory or the internet.

4. The device of claim 1 or 2, wherein said memory includes an audio recorder in said housing for recording sounds within a range of said housing.

5. The device of claim 1 or 2, further including a camera provided in said housing and connected to said microprocessor for capturing images in view of said housing.

6. The device of claim 5, wherein said camera is a night vision camera.

7. The device of claim 1 or 2, further including a wireless remote earphone for the cellphone.

8. The device of claim 1 or 2, wherein said device is for downloading or transmitting, including wired or wireless transmission, to at least one separate device.

9. The device of claim 1 or 2, wherein said cellphone is a satellite phone.

10. The device of claim 1 or 2, wherein said data comprises sounds, images, words and emails.

11. The device of claim 1 or 2, wherein said housing includes a socket with an engagement element and a spring, and said memory includes a replaceable memory card with an engagement feature receivable in a said socket in said housing.

12. The device of claim 11, wherein said socket is adapted for accepting replaceable memory cards of different memory capacities.

13. The device of claim 1 or 2, further including an earphone jack connected to said microprocessor for receiving a wire plug from an earphone set comprising a speaker and a microphone.

14. The device of claim 1 or 2, wherein said cellphone includes a volume adjustment for adjusting the volume of a speaker of said cellphone.

15. The device of claim 1 or 2, further comprising a jack provided in said housing and connected to said microprocessor for selective hardwire connection of said microprocessor to a computer or other device for downloading and uploading the data between said computer or other device and said cellphone memory.

16. The mobile entertainment and communication device of claim 1 or 2, further including
   a global positioning system provided in said housing and operatively connected to said cellphone, said cellphone having at least one of (1) a voice controlled dialing of a specific remotely located telephone number or (2) an emergency call button for dialing said specific remotely located telephone number and thereby also activating said global positioning system for transmitting images or the position of said cellphone to said specific remotely located telephone.

17. The mobile entertainment and communication device of claim 16, wherein said specific remotely located telephone number is "911".

18. The mobile entertainment and communication device of claim 16, wherein said cellphone is adapted for voice controlled dialing of said cellphone to a plurality of remotely located telephones.

19. The mobile entertainment and communication device of claim 16, further including a wireless remote microphone and earpiece speaker for operably communicating with said cellphone.

20. The mobile entertainment and communication device of claim 16, further comprising:
   a camera in said housing operable for capturing continuing images within a range of said housing; and
   said camera operatively connected to said cellphone and said memory for selectively storing said continuing images captured by said camera.

21. The mobile entertainment and communication device of claim 16, further comprising a replaceable memory card socket provided in said cellphone housing for selectively receiving a replaceable memory card; and
   said memory card socket operatively connected to said cellphone, and said memory.

22. A mobile entertainment and communication device for communicating with the Internet and remotely located telephones, comprising:
   a cellphone having a portable housing of a size and weight for being handheld by a person and adapted for placing and receiving person-to-person telephone calls to and from remotely located telephones, said cellphone having a microphone and a speaker;
   an audible alarm including at least one of said speaker or a separate audible sound generator;
   an emergency button on said housing and operatively connected to said audible alarm for selectively operating said audible alarm in an emergency;
   a camera in said housing operable for capturing images within a range of said housing; and
   said camera operatively connected to said emergency button for recording images captured by said camera upon actuating of said emergency button.

23. The mobile entertainment and communication device of claim 22, further comprising an automatic dialer for automatically dialing at least one of "911" or other emergency telephone numbers.

24. The mobile entertainment and communication device of claim 23, wherein said dialer includes said emergency button.

25. The mobile entertainment and communication device of claim 23, wherein said automatic dialer for automatically dialing a telephone number is separately operable from said emergency button.

26. The mobile entertainment and communication device of claim 23, further including a global positioning system provided in said housing and operatively connected to said cellphone, said emergency button also activating said global positioning system for transmitting the position of said cellphone to at least one of the emergency telephone numbers.

27. A mobile entertainment and communication device for communicating with remotely located telephones, comprising:
   a cellphone having a portable housing of a size and weight for being handheld by a person and adapted for wirelessly placing and receiving person-to-person telephone calls to and from remotely located telephones and wirelessly accessing the Internet,
   said cellphone having a microphone, a display and a speaker;
   a camera in said housing operable for capturing still images and continuing images within a range of said housing;
   a memory in said housing operatively connected to said microphone for storing sounds within a range of said microphone and for storing said images captured by said camera;
   separate switches for separately operating said microphone for capturing sounds and said camera for capturing said still or continuing images; and
   said cellphone adapted for reproducing and uploading to the Internet at least one of continuing images or combined sounds and continuing images.

28. A mobile entertainment and communication device for communicating with remotely located telephones, comprising:
   a cellphone having a portable housing of a size and weight for being handheld by a person and adapted for placing and receiving person-to-person telephone calls to and from remotely located telephones, said cellphone having a microphone, a display and a speaker;
   a camera in said housing operable for capturing still images and continuing images within a range of said housing;
   a memory in said housing operatively connected to said microphone for storing sounds within a range of said microphone and for storing said images captured by said camera;
   separate switches for separately operating said microphone for capturing sounds and said camera for capturing said still or continuing images; and
   said cellphone adapted for reproducing at least one of continuing images or combined sounds and continuing images, wherein said separate switches are adapted for simultaneously operating said camera for capturing continuing images and operating said microphone for capturing sounds with the continuing images.

29. The mobile entertainment and communication device of claim 27 or 28, wherein said captured images and sounds are stored on said memory.

30. The mobile entertainment and communication device of claim 27 or 28, wherein said captured images and sounds are transmitted simultaneously by said cellphone to a remotely located telephone while being captured.

31. The mobile entertainment and communication device of claim 27 or 28, wherein said memory includes a replaceable memory card receivable in a socket in said housing.

32. A mobile entertainment and communication device for communicating with the Internet and remotely located telephones, comprising:
   a cellphone having a portable housing of a size and weight for being handheld by a person and adapted for wirelessly accessing the Internet and placing and receiving person-to-person telephone calls to and from remotely located telephones, said cellphone having a microprocessor, a microphone, a speaker and a display;
   a camera in said housing and operable to capture still images and real time continuing images within a range of said housing;
   the microphone operable for capturing sounds within a range of said housing;
   a memory operatively connected to said cellphone, said camera and said microprocessor for storing at least one of the images captured by said camera, the sounds captured by said microphone, images or sounds received from the remotely located telephone, or data received from the Internet;
   said cellphone adapted for wirelessly communicating with a remotely located telephone and/or the Internet (1) causing at least one of the currently captured images or sounds, the stored images or sounds or the stored Internet data to be transmitted by said cellphone to the remotely located telephone or the Internet and/or (2) causing said cellphone to receive and to at least one of record in the memory or supply to the speaker or display the sounds or images from the remotely located telephone or data from the Internet;

at least one separate switch for activating said recording, transmitting or receiving;

said Internet data including at least one of still images, moving images, sounds, words, text or audio-visual performances, including the combined sounds and images of such performances;

the speaker and the display adapted for playing the stored sounds and/or displaying the stored images from said memory;

a global positioning system provided in said housing and connected to said cellphone for transmitting in real time images or the position of said cellphone to a remotely located telephone or the Internet when said cellphone is telephonically connected to the remotely located telephone or the Internet;

said cellphone activating said camera or said microphone upon activation of said global positioning system for also transmitting at least one of images and sounds with or without said real time position to the remotely located telephone or the Internet; and a jack on said housing for a wired connection between said cellphone and at least one of a computer, a radio, a television or CD, DVD, VCR, tape or phonograph record player for at least one of downloading or uploading sounds or images therebetween.

33. The mobile entertainment and communication device of claim 32, further including a motion detector in said housing operable to detect movement and then cause said cellphone to dial a pre-selected telephone number.

34. The mobile entertainment and communication device of claim 33, wherein said motion detector detects movement of said housing.

35. The mobile entertainment and communication device of claim 32, further including a sound detector in said housing operable to detect a sound and then cause said cellphone to dial a pre-selected telephone number.

36. The mobile entertainment and communication device of claim 32, further including an acceleration sensor in said housing operable to detect acceleration and deceleration for causing said cellphone to dial a pre-selected telephone number.

37. The mobile entertainment and communication device of claim 32, further including a light sensor in said housing operable to detect a change in light for causing said cellphone to dial a pre-selected telephone number.

38. The mobile entertainment and communication device of claim 32, further comprising a replaceable memory card socket provided in said cellphone housing for selectively receiving a replaceable memory card; and said memory card socket operatively connected to said cellphone, and said memory.

39. A mobile entertainment and communication device for communication with the Internet and remotely located telephones, comprising:

a housing of a palm-held size;

a cellphone provided in said housing, said cellphone adapted for selectively and wirelessly connecting to at least one of the Internet or remotely located telephones and adapted for controlling selection of at least one of (1) downloading data or uploading data from or to the Internet or (2) downloading data to a computer or other electronic device and said cellphone having at least one of (1) voice controlled dialing, (2) a wireless earphone or (3) a wire connection jack earphone with a microphone, for hands-free operation of the cellphone;

a memory operatively connected to said cellphone;

a microprocessor operatively connected to said memory;

said microprocessor adapted for storing data to said memory that is received from the Internet or a remotely located telephone: and a display panel operatively connected to said microprocessor, said display panel adapted for reproducing images or other data from at least one of said memory or the Internet, said other data including at least one of moving images or combined sounds and moving images;

said cellphone having a microphone, a speaker, and a camera the data stored to the memory including sounds and images; and a sensor in said housing for activating at least one of said microphone or said camera upon sensing an activating characteristic and then causing said memory to record at least one of the sounds received by said microphone or images captured by said camera.

40. The mobile entertainment and communication device of claim 39, wherein said sensor detects at least one of motion, sound, light, infrared, images, acceleration, deceleration, heat, smoke, carbon monoxide or poisonous gas as the activating characteristic.

41. The mobile entertainment and communication device of claim 39 or 40, further comprising a replaceable memory card socket provided in said cellphone housing for selectively receiving a replaceable memory card; and said memory card socket operatively connected to said cellphone, said microphone, said speaker, said camera and said memory.

42. A mobile entertainment and communication device for communicating with the Internet and remotely located telephones, comprising:

a housing of a palm-held size;

a cellphone provided in said housing, said cellphone adapted for selectively and wirelessly connecting to at least one of the Internet or remotely located telephones and adapted for controlling selection of at least one of (1) downloading data or uploading data from or to the Internet or (2) downloading data to a computer or other electronic device and said cellphone having at least one of (1) voice controlled dialing, (2) a wireless earphone or (3) a wire connection jack earphone with a microphone, for hands-free operation of the cellphone;

a memory operatively connected to said cellphone;

a microprocessor operatively connected to said memory;

said microprocessor adapted for storing data to said memory that is received from the Internet or a remotely located telephone: and a display panel operatively connected to said microprocessor, said display panel adapted for reproducing images or other data from at least one of said memory or the Internet, said other data including at least one of moving images or combined sounds and moving images;

said cellphone having a microphone, a speaker, and a camera, the data stored to the memory including sounds and images; and a sensor in said housing for activating at least one of said microphone or said camera upon sensing an activating characteristic and then causing said cellphone to dial a pre-selected telephone number of a remotely located telephone and, transmitting the sounds received by said microphone or images captured by said camera to that remotely located telephone, wherein said sensor detects at least one of motion, sound, light, infrared, images, acceleration, deceleration, sound, heat, smoke, carbon monoxide or poisonous gas as the activating characteristic.

43. A mobile entertainment and communication device for communicating with the Internet and remotely located telephones, comprising:

a housing of a palm-held size;

a cellphone provided in said housing, said cellphone adapted for selectively and wirelessly connecting to the Internet and remotely located telephones and adapted for controlling selection of at least one of (1) downloading data or uploading data from or to the Internet or (2) downloading data to a computer or other electronic device and said cellphone having at least one of (1) voice controlled dialing, (2) a wireless earphone or (3) a wire connection jack earphone with a microphone, for hands-free operation of the cellphone;

a memory operatively connected to said cellphone;

a microprocessor operatively connected to said memory;

said microprocessor adapted for storing data to said memory that is received from the Internet and/or a remotely located telephone; and a display panel operatively connected to said microprocessor, said display panel adapted for reproducing images and/or other data from at least one of said memory or the Internet, said other data including at least one of moving images or combined sounds and moving images;

said cellphone having a microphone, a speaker, and a camera, the data stored to the memory including sounds and images, said microphone, speaker, camera and memory operatively connected to a said microprocessor; and a light sensor in said housing for detecting low ambient light levels, said light sensor operatively connected to said microprocessor.

44. The mobile entertainment and communication device of claim 43, wherein said camera includes a video camera and a night vision camera, said microprocessor causing operation of said night vision camera when said light sensor senses a very low ambient light level and said camera is operated.

45. The mobile entertainment and communication device of claim 43 or 44, further comprising a replaceable memory card socket provided in said cellphone housing for selectively receiving a replaceable memory card; and said memory card socket operatively connected to said cellphone, said microphone, said speaker, said camera and said memory.

46. A mobile entertainment and communication device for communicating with the Internet and remotely located telephones, comprising:

a housing of a palm-held size;

a cellphone provided in said housing, said cellphone adapted for selectively and wirelessly connecting to the Internet and remotely located telephones and adapted for controlling selection of at least one of (1) downloading data or uploading data from or to the Internet or (2) downloading data to a computer or other electronic device and said cellphone having at least one of (1) voice controlled dialing, (2) a wireless earphone or (3) a wire connection jack earphone with a microphone, for hands-free operation of the cellphone;

a memory operatively connected to said cellphone;

a microprocessor operatively connected to said memory;

said microprocessor adapted for storing data to said memory that is received from the Internet or a remotely located telephone; and a display panel operatively connected to said microprocessor, said display panel adapted for reproducing images or other data from at least one of said memory or the Internet, said other data including at least one of moving images or combined sounds and moving images;

said cellphone having a microphone and a speaker;

a camera in said housing operable for capturing images within a range of said housing the memory in said housing operatively connected to said microphone for storing sounds within a range of said microphone and for storing images from said camera;

a light sensor in said housing for detecting low ambient light levels;

at least one separate switch provided in said housing for separately operating said microphone for capturing sounds or said camera for capturing still images or moving images; and the microprocessor being in said housing and operably connected to said microphone, said speaker, said camera, said memory, said light sensor and said at least one separate switch, wherein said at least one separate switch is adapted for simultaneously operating said camera for capturing continuing images and operating said microphone for capturing sounds with the continuing images.

47. The mobile entertainment and communication device of claim 46, wherein said camera includes a video camera and a night vision camera, said microprocessor causing operation of said night vision camera when said light sensor senses a very low ambient light level.

48. The mobile entertainment and communication device of claim 46 or 47, wherein said captured images and sounds are transmitted simultaneously by said cellphone to a remotely located telephone while being captured.

49. The mobile entertainment and communication device of claim 46, wherein said memory includes a replaceable memory card receivable in a socket in said housing.

50. A mobile entertainment and communication device for communicating with remotely located telephones, comprising:

a cellphone having a portable housing of a size and weight for being handheld by a person and adapted for placing and receiving person-to-person telephone calls to and from remotely located telephones;

said cellphone having a microphone, a speaker, a camera and a memory for storing sounds and images;

a light sensor in said housing for detecting low ambient light levels for camera operation;

a global positioning system provided in said housing for transmitting the real time position of said cellphone to a remotely located telephone, said global positioning system being activated by at least one of (1) voice controlled dialing of an emergency service number, (2) dialing an emergency service number, or (3) an emergency button that dials an emergency service number;

said cellphone activating said camera or said microphone upon activation of said global positioning system for also transmitting at least one of sounds, still images or moving images with said real time position to the remotely located telephone;

a microprocessor in said cellphone and operably connected to said light sensor and global positioning system;

at least one of (1) a jack connection on said housing for a wired connection between said cellphone and an earpiece speaker and a microphone or (2) a wireless earpiece, for hands-free use of said cellphone;

said microprocessor selectively operating at least one of said camera for capturing continuing images or said microphone for capturing sounds, said captured images or sounds being stored on said memory or transmitted to a remotely located telephone; and said microprocessor displaying images or emitting sounds stored on said memory or received from a remotely located telephone;

a sound detector in said housing operable to detect a sound and then cause said cellphone to dial a pre-selected telephone number.

51. A mobile entertainment and communicating device for communicating with the Internet and remotely located telephones, comprising:

a cellphone having a portable housing of a size and weight for being handheld by a person and adapted for at least one of wirelessly accessing the Internet or placing and receiving person-to-person telephone calls to and from remotely located telephones, said cellphone having a microphone, a speaker, a memory card socket and a display;

a camera in said housing and operable to capture still and real time continuing images within a range of said housing;

said microphone in said housing operable for capturing sounds within a range of said housing;

a memory including a replaceable memory card receivable in the socket in said housing and operatively connected to said cellphone, said camera and said microphone for selectively storing at least one of images captured by said camera, sounds captured by said microphone, images or sounds received from the remotely located telephone, or data received from the Internet;

a global positioning system provided in said housing and connected to said battery and cellphone for transmitting the position of said cellphone to a remotely located telephone;

a control switch for activating said cellphone for wirelessly communicating with a remotely located telephone or the Internet and, either (1) causing at least one of the captured images or sounds, the stored images or sounds or the stored Internet data to be transmitted by said cellphone to the remotely located telephone or the Internet or (2) causing said cellphone to receive and to at least one of record in the memory or supply to the speaker and display the sounds or images from the remotely located telephone or data from the Internet;

said Internet data including at least one of still images, moving images, sounds, words, text or audio-visual performances, including the combined sounds and images of such performances;

the speaker and the display adapted for playing the stored sounds or displaying the stored images from said memory.

52. The mobile entertainment and communication device of claim 50 or 51, further including a motion detector in said housing operable to detect movement and then cause said cellphone to dial a pre-selected telephone number.

53. The mobile entertainment and communication device of claim 51, further including a sound detector in said housing operable to detect a sound and then cause said cellphone to dial a pre-selected telephone number.

54. The mobile entertainment and communication device of claim 50 or 51, further including an acceleration sensor in said housing operable to detect acceleration and deceleration for causing said cellphone to dial a pre-selected telephone number.

55. A mobile entertainment and communication device for communicating with the Internet and remotely located telephones, comprising:

a housing of a palm-held size;

a cellphone provided in said housing and adapted for selectively and wirelessly connecting to the Internet and the remotely located telephones, said cellphone having a microphone, a speaker, a memory, a microprocessor, a display, a wired or wireless earphone, said cellphone further adapted for reproducing data;

a jack provided in said housing and operatively connected to said microprocessor for uploading data or downloading data between said cellphone and a computer and other devices;

said data including at least one of still images, moving images, sounds, words, text or audio-visual performances, including the combined sounds and images of such performances; and the microprocessor provided in said housing for starting the playing of and causing at least one of skipping portions of sounds, equalizing sounds or balancing sounds of said reproduced data.

56. A mobile entertainment and communication device for communicating with remotely located telephones, comprising:

a cellphone having a portable housing of a size and weight for being handheld by a person and adapted for placing and receiving person-to-person telephone calls to and from remotely located telephones, said cellphone having a microphone and a speaker;

a camera in said housing operable for capturing still images and continuing images within a range of said housing;

a memory in said housing operatively connected to said microphone for storing sounds within a range of said microphone and for storing said images captured by said camera;

separate switches for separately operating said microphone for capturing sounds and said camera for capturing said still or continuing images: and said cellphone adapted for reproducing at least one of continuing images or combined sounds and continuing images, wherein said separate switches are adapted for simultaneously operating said camera for capturing continuing images and operating said microphone for capturing sounds with the continuing images:

the housing including a memory card socket;

said cellphone having a microprocessor provided in said housing, said memory including a replaceable memory card receivable in the socket;

a jack provided in said housing and operatively connected to said microprocessor for uploading data or downloading data between said cellphone and a computer or other devices; and at least one of (1) an earphone and microphone with a wire for connecting to a jack in the housing of said cellphone, (2) a wireless earphone separate from said housing for receiving sounds from said cellphone, or (3) voice controlled dialing, each for hands-free cellphone operation.

57. The device of claim 1, 2, 22, 27, 32, 39, 42, 43, 46, 50, 51 or 56, wherein said cellphone is adapted for reproducing data, said recorded data including at least one of still images, moving images, sounds, words, text or audio-visual performances, including the combined sounds and images of such performances and for starting the playing of and causing at least one of skipping portions, equalizing sounds or balancing sounds of said reproduced data.

58. The device of claim 22, 27, 32, 39, 42, 43, 46, 50, 51 or 55, further including a wireless remote earphone for the cellphone that is separate from the cellphone.

59. The device of claim 55, wherein the housing includes a memory card socket, and said memory includes a replaceable memory card receivable in said socket in said housing.

60. The device of claim 56 or 59, wherein said socket is adapted for accepting replaceable memory cards of different memory capacities.

61. A mobile entertainment and communication device for communicating with the Internet and remotely located telephones, comprising:
a cellphone having a portable housing of a size and weight for being handheld by a person and adapted for wirelessly accessing the Internet and placing and receiving telephone calls to and from remotely located telephones, said cellphone having a microphone, a speaker, a camera and a memory for storing sounds captured by the microphone and still and moving images captured by the camera;
said memory including a replaceable memory card receivable in a socket in said housing and with either prerecorded data or no data on said replaceable memory card;
a microprocessor for controlling said cellphone for wirelessly communicating with at least one of the Internet or the remotely located telephone and (1) causing at least one of the sounds captured by the microphone or the moving images captured by the camera to be transmitted to at least one of the remotely located telephone or the Internet and/or (2) causing at least one of sounds or images to be received by said cellphone from at least one of the remotely located telephone or the Internet;
said cellphone having a display for displaying at least one of (1) said moving images captured by the camera, (2) moving images stored in the memory, including the replaceable memory card, or (3) moving images received from the remotely located telephone or the Internet and being capable of playing music with or without moving images;
at least one of (1) an earphone and microphone with a wire for connecting to a jack on said cellphone or (2) a wireless earphone separate from said cellphone housing for receiving sounds from said cellphone, each said earphone usable for receiving sounds from the remotely located telephone and at least one of the Internet, a music player, a radio or the memory, including the replaceable memory card.

62. The mobile entertainment and communication device of claim 61, wherein said microprocessor controlling each of (1) at least one of the sounds captured by the microphone or the moving images captured by the camera to be transmitted to at least one of the remotely located telephone or the Internet and (2) at least one of sounds or images to be received by said cellphone from at least one of the remotely located telephone or the Internet.

63. The mobile entertainment and communication device of claim 61 or 62, wherein said cellphone display is operable for displaying each of (1) said images captured by the camera, (2) images stored in the memory, including the replaceable memory card, and (3) images received from the remotely located telephone or the Internet.

64. A mobile entertainment and communication device for communicating with the Internet and remotely located telephones, comprising:
a housing of a palm-held size;
a cellphone provided in said housing and adapted for selectively and wirelessly connecting to the Internet and remotely located telephones;
a memory operatively connected to said cellphone;
a microprocessor provided in said cellphone and operatively connected to said memory;
said microprocessor adapted for storing data to said memory that is received from at least one of the Internet or a remotely located telephone;
a display and a speaker provided with said housing and operatively connected to said microprocessor for reproducing data from at least one of said cellphone, memory or the Internet; and
said microprocessor adapted for autocratically interrupting said reproducing of data during a telephone call from a one of the remotely located telephones:
said cellphone having a microphone, the speaker and the memory for storing sounds including a memory card socket in the portable housing;
said memory including a replaceable memory card directly receivable in said socket in said housing and with either prerecorded data or no data on said replaceable memory card, the memory card having a shape exhibiting asymmetry for causing proper orientation of said memory card in the socket and an engagement feature for use in securing the memory card in the socket;
a control switch and the microprocessor for activating said cellphone for wirelessly communicating with at least one of the Internet or the remotely located telephone and causing at least one of (1) transmitting the sounds captured by the microphone to at least one of the remotely located telephone or the Internet or (2) receiving the sounds by said cellphone from at least one of the remotely located telephone or the Internet and being capable of playing music;
at least one of (1) an earphone and microphone with a wire for connecting to a jack on said cellphone or (2) a wireless earphone separate from said cellphone housing for receiving sounds from said cellphone, each said earphone usable for receiving sounds from the remotely located telephone and at least one of the Internet or the memory, including the replaceable memory card.

65. The mobile entertainment and communication device of claim 64, wherein said control switch and microprocessor is are operable for causing each of (1) transmitting the sounds captured by the microphone to at least one of the remotely located telephone or the Internet or (2) receiving the sounds by said cellphone from at least one of the remotely located telephone or the Internet.

66. A mobile entertainment and communication device for communicating with the Internet and remotely located telephones, comprising:
a cellphone having a portable housing of a size and weight for being handheld by a person and adapted for wirelessly accessing the Internet and/or placing and receiving person-to-person telephone calls to and from remotely located telephones, said cellphone having a microphone, a memory for storing data and an audio recorder provided in the cellphone for recording sounds without a phone call, the recorded sounds being downloadable to at least one of a computer, television or other electronic device, said housing including a memory card socket;

said memory including a replaceable memory card receivable in said socket in said housing and with either prerecorded data or no data on said replaceable memory card;

a microprocessor controlling at least one of (1) wirelessly transmitting and receiving data to and from a remotely located telephone, (2) uploading or downloading data to and from the Internet, (3) reproducing data from said memory, including said replaceable memory card, or (4) reproducing data being received by said cellphone;

said reproducing data including at least one of moving images or combined sounds and moving images; and at least one of (1) an earphone and microphone with a wire for connecting to a jack on said cellphone or (2) a wireless earphone separate from said cellphone housing for receiving sounds from said cellphone, each said earphone usable for receiving sounds from the remotely located telephone and at least one of a radio, a music player, the Internet or the memory, including the replaceable memory card.

67. The mobile entertainment and communications device of claim 66, wherein said cellphone includes a microprocessor operable for causing at least two of the four functions of (1) wirelessly transmitting and receiving data to and from a remotely located telephone, (2) uploading or downloading data to and from the Internet, (3) reproducing data from said memory, including said replaceable memory card, or (4) reproducing data being received by said cellphone.

68. The mobile entertainment and communications device of claim 67, wherein said cellphone includes a microprocessor operable for causing at least three of the four functions of (1) wirelessly transmitting and receiving data to and from a remotely located telephone, (2) uploading or downloading data to and from the Internet, (3) reproducing data from said memory, including said replaceable memory card, or (4) reproducing data being received by said cellphone.

69. The mobile entertainment and communications device of claim 66, wherein, said cellphone includes a microprocessor operable for causing each of the four functions of (1) wirelessly transmitting and receiving data to and from a remotely located telephone, (2) uploading or downloading data to and from the Internet, (3) reproducing data from said memory, including said replaceable memory card, and (4) reproducing data being received by said cellphone.

70. A mobile entertainment and communication device for communicating with the Internet and a remotely located telephone, comprising:

a cellphone having a portable housing of a size and weight for being handheld by a person for wirelessly accessing the Internet and wirelessly placing and receiving person-to-person telephone calls to and from remotely located telephones, said cellphone having a microphone, a speaker, a microprocessor, a memory for storing sounds and an audio recorder provided in the cellphone for recording sounds without a phone call, the recorded sounds being downloadable to at least one of a computer, television or other electronic device;

said microprocessor controlling the playing of sound and at least one of controlling sound volume, skipping portions of sounds, equalizing sounds or balancing sounds; and at least one of (1) an earphone and microphone with a wire for connecting to a jack on said cellphone or (2) a wireless earphone separate from said cellphone housing for receiving sounds from said cellphone, each said earphone usable for receiving sounds from the remotely located telephone and at least one of the Internet, the a music player, the a radio or the memory.

71. The mobile entertainment and communication device of claim 70, wherein said housing includes a memory card socket, said memory includes a replaceable memory card receivable in said socket in said housing, and said replaceable memory card has prerecorded music playable by said cellphone.

72. A mobile entertainment and communication device for communicating with the Internet and remotely located telephones, comprising:

a housing of a palm-held size including a memory card socket;

a cellphone provided in said housing and adapted for selectively and wirelessly connecting to the Internet and/or remotely located telephones, a display and a speaker;

a memory operatively connected to said cellphone and including a replaceable memory card directly receivable in said socket in said housing, said replaceable memory card having either prerecorded data or no data;

a microprocessor provided in said cellphone and operatively connected to said memory;

said microprocessor adapted for storing data to said memory that is received from at least one of the Internet or a remotely located telephone;

said display and said speaker operatively connected to said microprocessor for reproducing data from at least one of said cellphone, memory or the Internet, said data including at least one of still images, moving images, sounds, words, text or audio-visual performances, including the combined sounds and images of such performances, wherein said combined sound and moving images reproduced at said housing includes visual entertainment;

a global positioning system provided in said housing and operatively connected to said microprocessor;

said cellphone having a dialer for dialing a remotely located telephone or the Internet and a control for activating said global positioning system for transmitting the position of said cellphone to the remotely located telephone or the Internet;

at least one of (1) a jack connection on said housing for a wired connection between said cellphone and said speaker as an earpiece speaker and a separate microphone, (2) said speaker as a speaker phone, or (3) voice controlled dialing, each for hands-free cellphone operations;

said microprocessor controlling at least one of sound play, controlling sound volume, skipping portions of sounds, equalizing sounds or balancing sounds provided by said at least one of a music player or a radio.

73. A mobile entertainment and communication device for communicating with the Internet and remotely located telephones, comprising:

a housing of a palm-held size including a memory card socket;

a cellphone provided in said housing and adapted for selectively and wirelessly connecting to the Internet and/or remotely located telephones;

a memory operatively connected to said cellphone and including a replaceable memory card receivable in said socket, said replaceable memory card having either prerecorded data or no data;

a microprocessor provided in said cellphone and operatively connected to said memory;

said microprocessor controlling storing data to said memory that is received from at least one of the Internet or a remotely located telephone when said cellphone is wirelessly connected to the Internet or a remotely located telephone;

a control switch provided with said housing and operatively connected to said microprocessor for reproducing data from at least one of said cellphone, memory or the Internet, said data including at least one of moving images or combined sound and moving images, wherein said combined sound and moving images reproduced at said housing includes visual entertainment;

a global positioning system provided in said housing and operatively connected to said microprocessor;

said cellphone adapted for dialing a remotely located telephone or the Internet and activating said global positioning system for transmitting the position of said cellphone to the remotely located telephone or the Internet;

said microprocessor controlling the playing of sound and at least one of controlling sound volume, skipping portions of sounds, equalizing sounds or balancing sounds provided by at least one of a music player and a radio.

74. A mobile entertainment and communication device for communicating with the Internet and remotely located telephones, comprising:

a cellphone having a portable housing of a size and weight for being handheld by a person and adapted for wirelessly connecting to the Internet and for placing and receiving person-to-person telephone calls to and from remotely located telephones, said cellphone having a microphone, a speaker, a memory card socket in said housing and a memory, said memory including a replaceable memory card receivable in said socket in said housing;

at least one of (1) an earphone and microphone with a wire for connecting to a jack on said cellphone or (2) a wireless earphone separate from said cellphone housing for receiving sounds from said cellphone, each said earphone usable for receiving sounds from the remotely located telephone and at least one of the Internet, a music player, a radio or the memory, including the replaceable memory card;

at least one control switch causing the playing of sound and at least one of controlling sound volume, skipping portions of sounds, equalizing sounds or balancing sounds provided to at least one of said cellphone speaker or each said earphone; and a display and a speaker provided in said housing for reproducing at least one of moving images or combined sounds and moving images from at least one of the Internet or the memory, including the replaceable memory card.

75. The mobile entertainment and communication device of claim 74, further including a jack connection on said housing for a wired connection between said cellphone and a separate device for downloading or uploading data therebetween, said separate device is at least one of a computer or a television.

76. A mobile entertainment and communication device for communicating with the Internet and remotely located telephones, comprising: a housing of a palm-held size;

a cellphone provided in said housing and adapted for selectively and wirelessly connecting to the Internet and remotely located telephones;

a memory operatively connected to said cellphone;

a microprocessor provided in said cellphone and operatively connected to said memory;

said microprocessor adapted for storing data to said memory that is received from at least one of the Internet or a remotely located telephone;

a display and a speaker provided with said housing and operatively connected to said microprocessor for reproducing data from at least one of said cellphone, memory or the Internet; and said microprocessor adapted for automatically interrupting said reproducing of data during a telephone call from a one of the remotely located telephones.

77. A mobile entertainment and communication device for communicating with the Internet and remotely located telephones comprising:

a camera and a cellular telephone electrically connected and mounted in a portable housing of a size and weight for being handheld by a person, said cellular telephone having a microprocessor, a microphone, a speaker, a display panel, a dial pad and at least one of a wired or wireless earpiece for use by the person for wireless accessing the Internet and for placing and receiving person-to-person telephone calls to and from remotely located telephones;

said microprocessor adapted for activating said camera and microphone for capturing images and sounds within a range of said housing;

a memory in said housing operatively connected to said camera and said cellular telephone for storing said images captured by said camera and said sounds captured by said microphone;

said cellphone adapted for causing at least one of said stored images or said stored sounds to be transmitted by said cellular telephone to at least one of a remotely located telephone or the Internet;

said memory including an audio recorder mounted in said housing and having means for recording audible transmissions during the person-to-person telephone calls to and from said cellular telephone and for recording sounds within a range of said housing without a telephone call;

a display and a speaker provided with said portable housing for reproducing sounds and images from said memory and the Internet;

at least one switch provided with the cellphone for downloading data from or uploading data to the Internet or downloading data to a computer or other devices; and a switch for separately operating at least one of (a) said microprocessor adapted for activating said camera, (b) said microphone, (c) said cellular telephone, (d) said memory, (e) said cellphone for causing said stored images and sounds to be transmitted, (f) said audio recorder, or (g) said display and speaker.

78. A mobile entertainment and communication device for communicating with the Internet and remotely located telephones, comprising:

a housing of a palm-held size;
a cellphone provided in said housing and adapted for selectively and wirelessly connecting to the Internet and remotely located telephones;
a memory operatively connected to said cellphone;
a microprocessor provided in said cellphone and operatively connected to said memory;
said microprocessor adapted for storing data to said memory that is received from at least one of the Internet or a remotely located telephone;
a display and a speaker provided with said housing and operatively connected to said microprocessor for reproducing data from at least one of said cellphone, memory or the Internet; and
said microprocessor adapted for autocratically interrupting said reproducing of data during a telephone call from a one of the remotely located telephones;
said cellphone having a microphone, the speaker, the display, a camera, the microprocessor and the memory for storing or reproducing data; and
at least one separate switch provided with the cellphone (1) for capturing real time moving images and sounds by said camera and microphone, (2) for reproducing real time moving images and sounds by said display and speaker, or (3) for downloading or uploading data between the cellphone and a computer and other devices.

79. The mobile entertainment and communication device of claim 27, 39, 42, 43, 46, 55, 56, 61, 64, 66, 70, 74, 76, 77 or 78, further including a global positioning system provided in said housing and operatively connected to said cellphone, said global positioning system being activated by at least one of (1) a voice controlled dialing of a specific number of a remotely located telephone or the Internet, (2) dialing said specific number of a remotely located telephone or the Internet, or (3) an emergency call button for dialing said specific number of a remotely located telephone or the Internet for transmitting the position of said cellphone to said remotely located telephone or the Internet.

80. The mobile entertainment and communication device of claim 1, 2, 27, 32, 39, 42, 46, 50, 51, 55, 61, 66, 72, 73, 74 or 77, wherein the sounds, images or data being received, transmitted or reproduced comprises combined sound and image data received, transmitted or reproduced simultaneously.

81. The mobile entertainment and communication device of claim 42, 50, 51, 74, 76, 77 or 78, wherein said memory includes a replaceable memory card receivable in a socket in said housing, said replaceable memory card having one of prerecorded data and no data.

82. The mobile entertainment and communication device of claim 1, 2, 22, 27, 43, 46, 55, 56, 61, 64, 66, 70, 72, 73, 74, 76, 77 or 78, further including at least one sensor for detecting at least one of motion, sound, light, infrared, images, acceleration, deceleration, heat, smoke, carbon monoxide or poisonous gas and, when such is detected, activating said cellphone to at least one of dialing an emergency service number or recording sound or images.

83. The mobile entertainment and communication device of claim 1 or 2, wherein said microprocessor is adapted for interrupting said reproducing of data during a telephone call from a one of the remote telephones.

84. The mobile entertainment and communication device of claim 50 wherein said microprocessor is adapted for interrupting said displaying of images or emitting of sounds during a telephone call to or from said cellphone.

85. The mobile entertainment and communication device of claim 32 or 51, wherein said cellphone is further adapted for interrupting said playing of the stored sounds or displaying of the stored images during a telephone call to or from said cellphone.

86. The mobile entertainment and communication device of claim 61, 64, 66 or 74, wherein said cellphone is further adapted for interrupting said receiving of sounds by each said earphone during a telephone call to or from said cellphone.

87. The mobile entertainment and communication device of claim 1, 2, 50, 51, 73, 74 or 78, further including a jack connection on said housing for a wired connection between said cellphone and a computer or other devices for downloading or uploading data from or to said cellphone.

88. The mobile entertainment and communication device of claim 50 or 51 further including separate switches provided with the housing (1) for capturing real time moving images and sounds by said camera and microphone, (2) for reproducing real time moving images and sounds by said display and speaker, and (3) for downloading or uploading data between the cellphone and a computer and other devices.

89. The mobile entertainment and communication device of claim 1, 2, 27, 39, 42, 43, 46, 50, 55, 56, 62, 64, 66, 70, 72, 73, 74, 76, 77 or 78, including a connector between said cellphone and at least one of a computer or other devices for downloading data from said cellphone to the computer or other devices.

90. A mobile entertainment and communication device for communicating with remotely located telephones, comprising: a portable housing of a palm-held size;
a cellphone provided in said housing and adapted for selectively and wirelessly connecting to remotely located telephones and the Internet;
a memory provided in said housing and operatively connected to said cellphone;
a memory card socket provided in said housing for receiving a replaceable memory card with substantially the entire card positioned within said housing, said replaceable memory card being of a substantially rectangular shape having four corners with at least one corner of an irregular shape different than the other corners; and
said memory card socket having at least one corner of an irregular shape that will receive said irregularly shaped corner of said replaceable memory card but not the other corners of said replaceable memory card upon inserting said replaceable memory card into said replaceable memory card socket for properly orienting said card in said socket.

91. A mobile entertainment and communication device for communicating with the Internet and remotely located telephones, comprising:
a housing of a palm-held size;
a cellphone provided in said housing and adapted for selectively and wirelessly connecting to the Internet and remotely located telephones and adapted for controlling selection of at least one of (1) downloading data or uploading data from or to the Internet or (2) downloading data to a computer or other electronic device and said cellphone having at least one of (1) voice controlled dialing, (2) a wireless earphone or (3) a wire jack earphone with a microphone, for hands-free operation of the cellphone;
a memory operatively connected to said cellphone;
a microprocessor operatively connected to said memory;

said microprocessor adapted for storing data to said memory that is received from the Internet or a remotely located telephone; and a display panel operatively connected to said microprocessor, said display panel adapted for reproducing images or other data from at least one of said memory or the Internet, said other data including at least one of moving images or combined sound and moving images;

the memory including a replaceable memory card;

a memory card socket provided in said housing for receiving the replaceable memory card with substantially the entire card positioned within said housing; and said replaceable memory card having at least one hole for use in securing said card in said memory card socket.

92. The mobile entertainment and communication device of claim 61, 64, 72, 73, 74 or 91; wherein said replaceable memory card is of a substantially rectangular shape having four corners with at least one corner of an irregular shape different than the other corners;

said socket has at least one corner of an irregular shape that will receive said irregular shaped corner of said replaceable memory card but not the other corners of said replaceable memory card upon inserting said replaceable memory card into said socket for properly orienting said card in said socket; and said replaceable memory card socket is capable of receiving replaceable memory cards having different memory capacities.

93. A mobile entertainment and communication device for communicating with remotely located telephones, comprising;

a portable housing of a palm-held size including an engagement element;

a cellphone provided in said housing and adapted for selectively and wirelessly accessing at least one of the Internet or remotely located telephones;

a memory provided in said housing and operatively connected to said cellphone, said memory including a replaceable memory card having a shape exhibiting asymmetry for causing proper orientation of said memory card in said housing, at least one engagement feature for receiving said engagement element and prerecorded data comprised of either combined sounds and text or combined sounds and moving images or no data;

a memory card socket in said housing for directly receiving said replaceable memory card with substantially the entire card positioned within said housing and secured in the replaceable memory card socket and said replaceable memory card socket being provided with a spring bearing directly against the memory card when in place in the memory card socket for urging the replaceable memory card out of the socket.

94. A mobile entertainment and communication device for communicating with the Internet and remotely located telephones, comprising:

a cellphone having a portable housing of a size and weight for being hand-held by a person and adapted for wirelessly accessing the Internet and placing and receiving person-to-person telephone calls to and from remotely located telephones, said cellphone having a microphone, a speaker, a camera and a memory for storing sounds captured by the microphone and still and moving images captured by the camera;

said memory including a replaceable memory card receivable in a replaceable memory card socket in said housing with substantially the entire memory card positioned within said housing and with either prerecorded data or no data on said replaceable memory card, said data including sounds and at least one of moving images or combined sounds and moving images;

said replaceable memory card having an irregularly shaped portion for mating with a similarly irregularly shaped portion of said replaceable memory card socket for properly orienting said memory card in said memory card socket;

said memory card socket adapted for accepting replaceable memory cards of different memory capacities;

said cellphone adapted for wirelessly communicating with at least one of the Internet or the remotely located telephone and (1) causing at least one of the sounds captured by the microphone or the moving images captured by the camera to be transmitted to at least one of the remotely located telephone or the Internet or (2) causing at least one of sounds or images to be received by said cellphone from at least one of the remotely located telephone or the Internet;

at least one separate switch provided for controlling downloading or uploading data from and to the Internet or downloading data to a computer or other devices;

said cellphone having a display for displaying at least one of (1) said images captured by the camera, (2) images stored in the memory, including the replaceable memory card, or (3) images received from the remotely located telephone or the Internet;

at least one of (1) an earphone and microphone with a wire for connecting to a jack on said cellphone or (2) a wireless earphone separate from said cellphone housing for receiving sounds from said cellphone, each said earphone usable for receiving sounds from at least one of the remotely located telephone, the Internet, a music player, a radio or the memory, including the replaceable memory card; and a control switch for causing at least one of playing sounds, controlling sound volume, skipping portions of sounds or data, equalizing sounds, or balancing sounds provided to at least one of said cellphone speaker or each said earphone.

95. A mobile entertainment and communication device for communicating with the Internet and remotely located telephones, comprising:

a cellphone having a portable housing of a size and weight for being hand-held by a person and adapted for wirelessly accessing the Internet and placing and receiving person-to-person telephone calls to and from remotely located telephones, said cellphone having a microphone, a speaker and a memory for storing sounds captured by the microphone, the housing having a memory card socket;

said memory including a replaceable memory card receivable in said socket and with either prerecorded data or no data on said replaceable memory card, said data including sounds and at least one of moving images or combined sounds and moving images;

said replaceable memory card having at least one corner of an irregular shape different than other corners of said memory card;

said replaceable memory card socket having at least one corner of an irregular shape that receives said irregularly shaped corner of said replaceable memory card;

said cellphone adapted for wirelessly communicating with at least one of the Internet or the remotely located telephone and causing at least one of (1) transmitting the sounds captured by the microphone to at least one of the remotely located telephone or the Internet or (2) receiving the sounds by said cellphone from at least one of the remotely located telephone or the Internet;

at least one separate switch provided with said cellphone for controlling downloading or uploading data from and to the Internet or downloading data to a computer or other devices;

at least one of (1) an earphone and microphone with a wire for connecting to a jack on said cellphone or (2) a wireless earphone separate from said cellphone housing for receiving sounds from said cellphone, each said earphone usable for receiving sounds from at least one of the remotely located telephone, the Internet or the memory, including the replaceable memory card; and a control switch provided in said housing for causing at least one of playing sounds, controlling sound volume, skipping portion of sounds or data, equalizing sounds or balancing sounds provided to at least one of said cellphone speaker or each said earphone.

96. A mobile entertainment and communication device for communicating with the Internet and remotely located telephones, comprising:

a cellphone having a portable housing of a size and weight for being handheld by a person and adapted for wirelessly accessing the Internet and placing and receiving person-to-person telephone calls to and from remotely located telephones, said cellphone having a microphone, a speaker and a memory for storing data, said housing having a memory card socket;

said memory including a replaceable memory card directly receivable in said memory card socket in said housing and with either prerecorded data or no data on said replaceable memory card, with substantially the entire replaceable memory card directly positioned within the cellphone and including a memory card engagement device and a spring in direct contact with the replaceable memory card for urging the replaceable memory card out of the socket upon release of the memory card engagement device;

said replaceable memory card socket adapted for accepting replaceable memory cards of different memory capacities;

at least one separate switch provided with said cellphone for controlling uploading or downloading data to or from the Internet or downloading data to a computer or other devices;

said cellphone operable for causing at least one of (1) wirelessly transmitting and receiving data to and from a remotely located telephone, (2) uploading or downloading data to and from the Internet, (3) reproducing data from said memory, including said replaceable memory card, or (4) reproducing data being received by said cellphone;

said data including at least one of still images, moving images, sounds, words, text or audio-visual performances, including the combined sounds and images of such performances; and at least one of (1) an earphone and microphone with a wire for connecting to a jack on said cellphone or (2) a wireless earphone separate from said cellphone housing for receiving sounds from said cellphone, each said earphone usable for receiving sounds from at least one of the remotely located telephone, the Internet or the memory, including the replaceable memory card; and a control switch provided in said housing for causing at least one of playing sounds, controlling sound volume, skipping portions of sounds or other data, equalizing sounds or balancing sounds provided to at least one of said cellphone speaker or each earphone.

97. A mobile entertainment and communication device for communicating with the Internet and a remotely located telephone, comprising:

a housing of palm-held size;

a cellphone provided in said housing and adapted for wirelessly connecting to the Internet and remotely located telephones, said cellphone having a memory;

said cellphone memory including a replaceable memory;

a replaceable memory card socket provided in said housing for directly receiving said replaceable memory card with substantially the entire card positioned within said housing and secured in the replaceable memory card socket;

a memory card engagement device and a spring in direct contact with the replaceable memory card for urging the replaceable memory card out of the socket upon release of the memory card engagement device;

a microprocessor provided in said cellphone and operatively connected to said memory and said replaceable memory card;

said microprocessor adapted for storing data to said memory or replaceable memory card that is received from the Internet or a remotely located telephone;

a display and a speaker provided with said housing and operatively connected to said microprocessor for reproducing data from at least one of said cellphone, said memory, said replaceable memory card or the Internet, said cellphone further adapted for at least one of playing sounds, controlling sound volume, skipping a portion of sounds or images and data, or equalizing sounds;

at least one separate switch provided with said cellphone for controlling downloading data or uploading data from and to the Internet or downloading data to a computer or other devices;

at least one of (1) an earphone and microphone with a wire for connecting to a jack on said cellphone or (2) a wireless earphone separate from said cellphone housing for receiving sounds from said cellphone, each said earphone usable for receiving sounds from at least one of the remotely located telephone, the Internet, a music player, with or without images, a radio, said memory, or said prerecorded replaceable memory card; and said data including at least one of still images, moving images, sounds, words, text, or audio-visual performance, including the combined sounds and images of such performances.

98. A mobile entertainment and communication device for communicating with the Internet and remotely located telephones, comprising:

a housing of a palm-held size;

a cellphone provided in said housing adapted for selectively and wirelessly connecting to the Internet and remotely located telephones, said housing including a replaceable memory card socket;

a memory operatively connected to said cellphone and including a replaceable memory card receivable in said memory card socket in said housing, said replaceable memory card having either prerecorded data or no data;

said replaceable memory card socket having at least one corner of an irregular shape that will receive at least one irregularly shaped corner of said replaceable memory card;

a microprocessor provided in said cellphone and operatively connected to said memory;

said microprocessor adapted for storing data to said memory that is received from at least one of the Internet or a remotely located telephone;

a display provided with said housing and operatively connected to said microprocessor for at least one of (1) simultaneously reproducing data received from the internet as data is received, or (2) reproducing data from at least one of said cellphone or memory;

at least one separate switch provided with said cellphone for controlling uploading data or downloading data to and from the Internet or downloading data to a computer or other devices;

at least one of (1) an earphone and microphone with a wire for connecting to a jack in said cellphone or (2) a wireless earphone separate from said cellphone housing for receiving sounds from said cellphone, each said earphone usable for receiving sounds from at least one of the remotely located telephone, the Internet, a music player, a radio or the memory, including the replaceable memory card; and a control switch provided in said housing for causing at least one of playing sounds, controlling sound volume, skipping portions of sounds, equalizing sounds or balancing sounds provided to at least one of said cellphone speaker or each said earphone.

99. A mobile entertainment and communication device for communicating with the Internet and remotely located telephones, comprising:

a housing of a palm-held size;

a cellphone provided in said housing and adapted for selectively and wirelessly connecting to the Internet and/or remotely located telephones, the housing including a memory card socket;

a memory operatively connected to said cellphone and including a replaceable memory card receivable in said memory card socket in said housing, said replaceable memory card having either prerecorded data or no data;

said memory card socket having at least one corner of an irregular shape that will receive at least one irregularly shaped corner of said replaceable memory card;

a microprocessor provided in said cellphone and operatively connected to said memory;

said microprocessor adapted for storing data to said memory that is received from at least one of the Internet or a remotely located telephone when said cellphone is wirelessly connected to the Internet or a remotely located telephone;

at least one separate switch provided with said cellphone for controlling uploading data or downloading a data to and from the Internet or downloading data to a computer and other devices;

said microprocessor adapted for reproducing data from at least one of said cellphone, said memory or the Internet, said reproducing of data including at least one of moving images or combined sound and moving images;

a global positioning system provided in said housing and operatively connected to said microprocessor;

said cellphone having a dialer for dialing a remotely located telephone or the Internet and activating said global positioning system for transmitting the position of said cellphone to the remotely located telephone or the Internet;

a control switch provided in said housing for causing at least one of playing sounds, controlling sound volume, skipping portions of sounds or other data, equalizing sounds or balancing sounds provided through said cellphone.

100. A mobile entertainment and communication device for communicating with remotely located telephones, comprising:

a cellphone having a portable housing of a size and weight for being handheld by from remotely located telephones, said cellphone having a microphone and a speaker;

a camera in said housing operable for capturing still images and continuing images within a range of said housing;

a memory in said housing operatively connected to said microphone for storing sounds within a range of said microphone and for storing said images captured by said Camera;

separate switches for separately operating said microphone for capturing sounds and said camera for capturing said still or continuing images; and said cellphone adapted for reproducing at least one of continuing images or combined sounds and continuing images, wherein said separate switches are adapted for simultaneously operating said camera for capturing continuing images and operating said microphone for capturing sounds with the continuing images;

said memory including a replaceable memory card;

at least one of (1) an earphone and microphone with a wire for connecting to a jack on said cellphone or (2) a wireless earphone separate from said cellphone housing for receiving sounds from said cellphone, each said earphone usable for receiving sounds from at least one of the remotely located telephone, the Internet, a music player, a radio or the memory, including the replaceable memory card;

a control switch provided in said housing for causing at least one of playing sounds, controlling sound volume, skipping portions of sounds or other data, equalizing sounds or balancing sounds provided to at least one of said cellphone speaker or each said earphone;

a memory card socket provided in said housing for receiving said replaceable memory card with substantially the entire card positioned within said housing and secured in the memory card socket, said memory card socket having at least one corner of an irregular shape that will receive at least one irregularly shaped corner of said replaceable memory card; and said replaceable memory card having at least one hole for use in securing said replaceable memory card in said memory card socket.

101. A mobile entertainment and communication device for communicating with the Internet and remotely located telephones, comprising:

a housing of a palm-held size;

a cellphone provided in said housing, said cellphone adapted for selectively and wirelessly connecting to the Internet and remotely located telephones and adapted for controlling selection of at least one of (1) downloading data or uploading data from or to the Internet or (2) downloading data to a computer or other electronic device and said cellphone having at least one of (1) voice controlled dialing, (2) a wireless earphone or (3) a wire connection jack earphone with a microphone for hands-free operation of the cellphone;
a memory operatively connected to said cellphone;
a microprocessor operatively connected to said memory;
said microprocessor adapted for storing data to said memory that is received from the Internet or a remotely located telephone; and
a display panel operatively connected to said microprocessor, said display panel adapted for reproducing images or other data from at least one of said memory or the Internet, said other data including at least one of moving images or combined sounds and moving images;
a replaceable memory card for replaceably installing directly in the cellphone, said memory card exhibiting asymmetry for causing proper orientation of said memory card in the cellphone, said memory card having at least one engagement feature for use in securing the memory card in the cellphone, wherein said replaceable memory card has prerecorded data comprised of either combined sounds and text or combined sounds and moving images or no data.

102. The mobile entertainment and communication device of claim 39 or 42 wherein there are at least two said sensors for detecting at least two of motion, sound, light, infrared, images, acceleration, deceleration, heat, smoke, carbon monoxide or poisonous gas as the activating characteristic.

103. The mobile entertainment and communication device of claim 39 or 42 wherein there are at least three said sensors for detecting at least three of motion, sound, light, infrared, images, acceleration, deceleration, heat, smoke, carbon monoxide or poisonous gas as the activating characteristic.

104. A mobile entertainment and communication device for communicating with remotely located telephones, comprising:
a housing of a palm-held size;
a cellphone provided in said housing and adapted for selectively and wirelessly accessing the remotely located telephones and the Internet;
said cellphone having a microphone, a speaker, a camera, a display, a memory and a microprocessor provided in said housing;
a sensor operatively connected to said microprocessor for detecting at least one activating characteristic of sound, motion, light, infrared or images and, upon such detection, activating said cellphone for capturing at least one of sounds or images, said cellphone then either recording to said memory or transmitting telephonically to a remotely located telephone or the Internet the captured said at least one of sounds and images;
said cellphone adapted for hands-free operation of said cellphone comprising at least two of (1) an earphone and microphone with a wire for connecting to said cellphone, (2) a wireless earphone separate from said housing adapted for communicating with said cellphone, (3) a voice control operating with said cellphone, or (4) automatic dialing of said cellphone to at least one of a pre-selected number or the Internet upon said sensor detecting the activating characteristic; and
at least one separate switch provided with said housing for starting the reproduction of data at said housing and controlling that reproduction by at least one of skipping portions of the data, equalizing sounds or controlling the volume of sounds, said data including at least one of still images, moving images, sounds, words, text, visual entertainment, or audio visual data combining sounds and images.

105. The mobile entertainment and communication device of claim 104 wherein there are at least two said sensors for detecting at least two of motion, sound, light, infrared, images, acceleration, deceleration, heat, smoke, carbon monoxide or poisonous gas as the activating characteristic.

106. A mobile entertainment and communication device for communicating with the Internet and remotely located telephones, comprising:
a housing of a palm-held size;
a cellphone provided in said housing, said cellphone adapted for selectively and wirelessly connecting to the Internet and remotely located telephones;
a memory operatively connected to said cellphone;
a microprocessor provided in said cellphone and operatively connected to said memory;
said microprocessor adapted for storing data to said memory that is received from the Internet or a remotely located telephone; and
a display and a speaker provided with said housing and operatively connected to said microprocessor for reproducing data from at least one of said cellphone memory or the Internet; and
said microprocessor adapted for automatically interrupting said reproducing of data during a telephone call from a one of the remotely located telephones;
said cellphone having a microphone, and a camera;
said cellphone adapted for causing the recording of at least one of (1) real time moving images or (2) combined real time sounds and moving images simultaneously;
at least one separate switch provided with said housing and cellphone for causing at least one of (1) recording real time sounds and moving images simultaneously, (2) reproducing at the housing sounds and moving images simultaneously, or (3) downloading at least one of still images, moving images, sounds or combined moving images and sounds to a computer, television or recording device;
a jack provided on said housing and operatively connected to said microprocessor for receiving a wire having an earphone for reproducing sound;
said display operatively connected to said microprocessor for reproducing the images; and
said memory recording the sounds and the images, including combined sounds and moving images, for allowing the reproduction of the sounds and images by the cellphone or by at least one of a computer, a television or a reproducing device.

107. The mobile entertainment and communication device of claim 106, further comprising, voice controlled dialing of said cellphone of pre-selected telephone numbers, including 911, for automatically transmitting at least sounds from the cellphone.

108. The mobile entertainment and communication device of claim 106, further comprising, at least one sensor in said housing operatively connected to said microprocessor for activating said microphone and cellphone upon said sensor sensing at least one activating characteristic of sounds, motion, light, infrared or images; and
upon said cellphone being activated by said sensor sensing an activating characteristic, said cellphone automatically causing at least one of (1) dialing a preselected telephone number and transmitting the sounds captured by said microphone to a remotely located telephone or (2) recording on said memory the sounds captured by said microphone.

109. The mobile entertainment and communication device of claim 106, further comprising, at least one sensor in said housing operatively connected to said microprocessor for activating said microphone, said camera and said cellphone upon said sensor sensing at least one activating characteristic of sounds, motion, light, infrared or images; and upon said cellphone being activated by said sensor sensing an activating characteristic, said cellphone automatically causing at least one of (1) dialing a preselected telephone and transmitting the sounds captured by said microphone and images captured by said camera to a remotely located telephone or (2) recording on said memory the sounds captured by said microphone and images captured by said camera.

110. The mobile entertainment and communication device of claim 108 or 109, wherein there are at least two said sensors for detecting at least two of sounds, motion, light, infrared or images as the activating characteristic.

111. The mobile entertainment and communication device of claim 1, further comprising a separate switch on said housing for causing the downloading or uploading of data.

112. A mobile entertainment and communication device for communicating with the Internet and remotely located telephones comprising:

a handheld cellphone for telephone calls and entertainment including an audio recorder, a video recorder, voice controlled dialing, a wired earphone with microphone, a microphone, a speaker, a display, a camera, a memory, a microprocessor, an emergency call function, said microprocessor adapted for causing operation of at least one of the camera or the microphone upon activation of the emergency call function for transmitting sound and at least one of still images, moving images, or combined sounds and moving images to a remotely located telephone.

113. A mobile entertainment and communication device for communicating with the Internet and remotely located telephones comprising:

a handheld cellphone for telephone calls and entertainment including an audio recorder, a video recorder, voice controlled dialing, a wired earphone with microphone, a microphone, a speaker, a display, a camera, a microprocessor, a memory, an emergency call function that dials a pre-selected emergency number activating the emergency call function, said microprocessor adapted for causing operation of at least one of the camera or the microphone upon activation of the emergency call function for transmitting sound and at least one of still images, moving images, or combined sounds and moving images.

114. The mobile entertainment and communication device for communicating with remotely located telephones by a cellphone of claim 91, 100 or 101, said housing comprising at least one engagement element for receiving at least one engagement feature of said replaceable memory card for use in directly securing and removing said memory card from the socket, said engagement feature comprising at least one hole.

115. The mobile entertainment and communication device of claim 91, 100 or 101, said memory card having at least one card corner having an irregular shape that is different from other card corners, the irregular shaped corner matching the shape of the socket when the entire card is positioned therein.

116. A mobile entertainment and communication device for communicating with remotely located telephones, comprising:

a portable housing of a palm-held size including an engagement element and a card socket;

a cellphone provided in said housing and adapted for selectively and wirelessly accessing the Internet and remotely located telephones;

a memory provided in said housing and operatively connected to said cellphone said memory including a replaceable memory card having a shape exhibiting asymmetry for causing proper orientation of said memory card in said housing, said card socket in said housing for directly receiving said replaceable memory card with substantially the entire card positioned within said housing, said memory card having at least one engagement feature for receiving said engagement element for use in securing and releasing said memory card, the memory card being capable of having different memory capacities without changing card size and card shape and capable of being inserted directly into the card socket without a change of socket dimensions when substantially the entire card is positioned within said housing said card for reproducing and storing data and having either prerecorded data or no/blank data, said prerecorded data comprised of either combined sounds and text, combined images and text, real time moving images, real time sounds and real time moving images or GPS location information.

117. A communication system comprising:

a handheld cell phone for telephone calls and wireless access to the Internet and including a microphone, a speaker, a display, a memory with a replaceable memory card, a microprocessor and a memory card socket for receiving said replaceable memory card, said memory card and memory card socket having complementary shapes exhibiting asymmetry for unique orientation of said memory card in said socket with substantially the entire memory card positioned directly within said socket;

at least one sensing system provided and operatively connectable to said microprocessor; said sensing system having at least one of (1) a camera for capturing still or moving images, (2) a microphone for capturing sounds capable of being sequenced with said camera or (3) at least one sensor for detecting at least one of (1) a sound, (2) images, 3) motion, (4) light, (5) infrared, (6) heat, (7) smoke, (8) carbon monoxide or (9) a poisonous gas, said microprocessor providing operation for capturing at least one of moving images or combined sound and moving images, and providing operation for at least one of (1) reproducing moving images and sounds through said display and said speaker or (2) loading data from or to said cell phone to or from one or more of the Internet or an electronic device.

118. A mobile entertainment and communication device comprising:

a handheld cellphone for telephone calls and wireless access to the Internet and including a microphone, a speaker, a display, a camera, a memory and a microprocessor, said microprocessor providing operation for selectively (1) capturing moving images, sounds or simultaneous sounds and moving images, (2) reproducing moving images by said display and sounds by said speaker separately or simultaneously, (3) loading data including sounds and moving images to and from the Internet or (4) loading data including sounds and moving images between said cellphone and an electronic device;

a remote wired or wireless earphone, said microprocessor providing operation for directing sounds to at least one of said earphone or said speaker from the telephone calls, said microprocessor further providing operation for handling data including sounds and moving images from at least one of said microphone, camera, internet or memory, said microprocessor further providing operation for causing at least one of playing sounds, controlling sound volume, skipping portions of the data, equalizing sounds or balancing sounds, said microprocessor further providing operation for automatically interrupting the playing of sound and images upon receiving a telephone call.

119. The mobile entertainment and communication device of claim 61, 70, 71, 72-73, 74, 94-95, 97-98, 99, 100 or 118, said cellphone further including a radio receiver in said cellphone housing playable through said speaker or a wired or wireless earphone.

120. A mobile entertainment and communication device for communicating with the Internet and remotely located telephones comprising:

a hand-held cellphone including a microphone, a speaker, a camera, memory, a microprocessor and at least three of (1) a wired remote microphone and earphone, (2) a wireless earphone, (3) a speaker as a speaker phone or (4) voice control activation, said microprocessor providing operation by voice controlled cellphone activation for selectively causing at least one of (1) capturing combined sounds and moving images by microphone and camera, (2) transmitting stored combined sounds and moving images to a pre-selected one or more of the remote telephones or (3) transmitting captured combined sounds and moving images to a pre-selected one or more of the remote telephones.

121. A mobile entertainment and communication device for communicating with the Internet and remotely located telephones comprising:

a housing of a palm-held size;

a cellphone provided in said housing and adapted for selectively and wirelessly connecting to the Internet and remotely located telephones, said cellphone having at least one of a microphone, a speaker, a memory, a microprocessor, a display, a wired or wireless earphone, voice controlled dialing, a jack, an interrupting, a socket, a GPS or an audio recorder, said cellphone further adapted for reproducing data from at least one of the memory or a replaceable memory card;

at least one of said wired or wireless earphone for mobile entertainment without phone calls;

said data including at least one of still images, moving images, sounds, words, text or music with or without images, or combined real time sounds and moving images; and the microprocessor provided in said housing and being adapted for starting the playing of and causing at least one of skipping a portion of sounds or other data, equalizing sounds, or balancing sounds of reproduced data.

122. A mobile entertainment and communication device for communicating with Internet or remotely located telephones, comprising;

a housing of a palm-held size;

a cellphone provided in said housing and adapted for selectively and wirelessly connecting to the Internet and remotely located telephones, and adapted for uploading data or downloading data to or from the Internet;

said cellphone having at least one of a microprocessor, a microphone, a display, a memory, a wired or wireless earphone, voice controlled dialing, a jack, an interrupting, a socket, a GPS or an audio recorder, said cellphone further adapted for reproducing data from at least one of the Internet, the cellphone memory, or a replaceable memory card;

at least one of said wired or wireless earphone for mobile entertainment without phone calls;

said data including at least one of still images, moving images, sounds, words, text or music with or without images, or combined real time sounds and moving images; and said microprocessor provided in said housing and adapted for starting the playing of and causing at least one of a skipping portion of data, equalizing sounds, or balancing sounds of reproduced data.

123. A mobile entertainment and communication device for communicating with the Internet and to a remotely located telephone, comprising;

a housing of a palm held-size;

a cellphone provided in said housing and adapted for selectively and wirelessly connecting to the Internet and the remotely located telephone;

said cellphone having at least one of a microprocessor, a microphone, a display, a camera a memory, a wired or wireless earphone, voice controlled dialing, an audio recorder, a jack, an interrupting, a socket, a GPS or a video recorder, and adapted for reproducing data from the memory and storing data to the memory;

at least one of said wired or wireless earphone for receiving music and/or sounds, for entertainment without phone calls;

said data including at least one of still images, moving images sounds, text, words, music with or without images, images with text or real time combined sounds and moving images simultaneously;

said microprocessor provided in said housing and adapted for starting the playing of and causing at least one of skipping a portion of data, equalizing sounds, or balancing sounds of reproduced data.

124. A mobile entertainment and communication device for communicating with Internet and remotely located telephones, comprising;

a housing of a palm-held size:

a cellphone provided in said housing and adapted for selectively and wirelessly connecting to the remotely located telephones or Internet, said cellphone having a card socket and a replaceable memory card;

said housing having at least one engagement element, wherein the memory card has a flat rectangular shape exhibiting asymmetry for causing proper orientation of the memory card in the housing and has at least one engagement feature for (1) receiving the engagement element, (2) securing the card in the card socket of the cellphone and (3) removing the card therefrom, the housing further comprising a spring in the card socket for urging the memory card out of the socket upon release of the memory card engagement element;

said replaceable memory card operatively connected to at least one of a microprocessor, a microphone, a speaker, or a wired or wireless earphone, for reproducing data from the replaceable memory card or storing data to the replaceable memory card;

said replaceable memory card for reproducing prerecorded data including controlling at least one of start playing data, balancing sounds, equalizing sounds or skipping data is controllable when reproducing data;

said replaceable memory card comprising either a prerecorded memory card or a blank memory card for performing at least one of (1) transmitting and/or downloading data to at least one separate remote device, (2) reproducing data, (3) recording data and (4) storing data, wherein said data of said memory card comprises real time sounds, still or moving images, music with or without moving images, combined sounds and moving images, combined sounds and text, or other data; and wherein the memory card comprises different memory capacities without changing card size and shape, and is capable of being inserted directly into the card socket of the cellphone when substantially the entire memory card is positioned in the card socket.

125. A mobile entertainment and communication device for communicating with Internet or remotely located telephones, comprising;

a housing of a palm-held size;

a cellphone provided in said housing and adapted for selectively and wirelessly connecting to the Internet and remotely located telephones, said cellphone having a memory including a replaceable memory card, said replaceable memory card replaceable directly in the cellphone, wherein said cellphone has a card socket for receiving the replaceable memory card;

said memory card having a flat, rectangular shape exhibiting asymmetry for causing proper orientation in association with the cellphone, and having at least one card corner having an irregular shape that is different from other card corners, the irregular shaped corner matching the shape of the card socket when the entire card is positioned therein;

said replaceable memory card having at lease one of engagement feature on the card for at least one of securing the card in the card socket or removing the card from the card socket;

said memory card having either prerecorded data or no/blank data for at least one of (1) down loading pre-recorded data to at least one separate device, (2) reproducing pre-recorded data, or (3) storing data to the card, said prerecorded data of said memory card including real time sounds and at least one of (1) real time moving images, (2) simultaneously combined sounds and moving images, (3) simultaneously combined sounds and texts, (4) music with or without images, or (5) other data, and also capable of storing at least one of real time sounds, still or moving images, music with or without moving images, combined sounds and moving images, combined sounds and text, or other data to the replaceable memory card; and wherein the card is capable of having different memory capacities without changing card size and card shape, and capable of inserting directly into the card socket of the cellphone without a change of socket dimensions when substantially the entire card is positioned in the card socket.

* * * * *

UNITED STATES PATENT AND TRADEMARK OFFICE
CERTIFICATE OF CORRECTION

PATENT NO. : 7,321,783 B2
APPLICATION NO. : 10/719363
DATED : January 22, 2008
INVENTOR(S) : Ki Il Kim It is certified that error appears in the above-identified patent and that said Letters Patent is hereby corrected as shown below:

On page 3 under "FOREIGN PATENT DOCUMENTS"
"GB 230875 7/1997" should read --GB 2308775 7/1997--;

Claim 32 (col. 8, line 67) delete "currently";

Claim 64 (col. 16, line 26) "autocratically" should read --automatically--;

Claim 65 (col. 16, line 58) "is are" should read --are--;

Claim 66 (col. 17, line 1) "and/or" should read --and--;

Claim 78 (col. 21, line 15) "autocratically" should read --automatically--;

Claim 82 (col. 21, line 53) "2, 22" should read --2, 20, 22--;

Claim 89 (col. 22, line 25) "62" should read --61--;

Claim 92 (col. 23, line 18) the semicolon ";" between "91" and "wherein" should be deleted; and Claim 125 (col. 36, line 10) "lease" should read --least--.

Signed and Sealed this

Tenth Day of June, 2008

JON W. DUDAS
*Director of the United States Patent and Trademark Office*

US007321783C1

(12) INTER PARTES REEXAMINATION CERTIFICATE (0456th)
United States Patent
Kim

(10) Number: US 7,321,783 C1
(45) Certificate Issued: Sep. 18, 2012

(54) MOBILE ENTERTAINMENT AND COMMUNICATION DEVICE

(75) Inventor: Ki Il Kim, Los Angeles, CA (US)

(73) Assignee: K-Technology USA, Inc., Pico Rivera, CA (US)

Reexamination Request:
No. 95/001,080, Sep. 9, 2008
No. 95/001,183, Apr. 29, 2009
No. 90/010,623, Jul. 28, 2009

Reexamination Certificate for:
Patent No.: 7,321,783
Issued: Jan. 22, 2008
Appl. No.: 10/719,363
Filed: Nov. 20, 2003

Certificate of Correction issued Jun. 10, 2008.

Related U.S. Application Data

(63) Continuation of application No. 09/531,356, filed on Mar. 20, 2000, now Pat. No. 6,681,120, which is a continuation-in-part of application No. 08/846,108, filed on Apr. 25, 1997, now Pat. No. 6,278,884.

(51) Int. Cl.
*H04M 1/00* (2006.01)
*H04B 1/38* (2006.01)
*H04Q 7/20* (2006.01)

(52) U.S. Cl. ............... 455/556.1; 455/557; 455/90.1; 348/E5.002; 348/E7.079; 348/E7.087; 348/E7.088

(58) Field of Classification Search ................. None
See application file for complete search history.

(56) References Cited

To view the complete listing of prior art documents cited during the proceedings for Reexamination Control Numbers 95/001,080, 95/001,183 and 90/010,623, please refer to the USPTO's public Patent Application Information Retrieval (PAIR) system under the Display References tab.

*Primary Examiner* — Mary Steelman

(57) ABSTRACT

A mobile entertainment and communication device in a palm-held size housing has a cellular or satellite telephone capable of wireless communication with the Internet and one or more replaceable memory card sockets for receiving a blank memory card for recording data directly from the Internet and, in particular, musical performances that then can be selectively reproduced by the device for the enjoyment of the user, including both audio and visual recordings and reproductions. The device also includes a camera and microphone for recording images and sound within the range of the device that can be wirelessly transmitted, either selectively or automatically to a remote telephone. Further, the device includes sensors for sensing unusual conditions that may also be transmitted to a remote telephone, together with the location of the device as determined by a GPS section of the device.

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-5, 7-8, 10-21, 27-36, 39-40, 42-43, 46, 49-51, 53, 55-56, 59-78, 83-86, 88, 90-101 and 104-125 are cancelled.

Claims 6, 9, 22-26, 37, 38, 41, 44, 45, 47, 48, 52, 54, 57, 58, 79, 80, 81, 82, 87, 89, 102 and 103 were not reexamined.

* * * * *